United States Patent
Wu et al.

(10) Patent No.: US 11,554,145 B2
(45) Date of Patent: Jan. 17, 2023

(54) THERAPEUTIC AND PROPHYLACTIC TREATMENT FOR COLORECTAL CANCER

(71) Applicant: The Chinese University of Hong Kong, Hong Kong (CN)

(72) Inventors: Ka Kei Wu, Hong Kong (CN); Jun Yu, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 122 days.

(21) Appl. No.: 16/750,985

(22) Filed: Jan. 23, 2020

(65) Prior Publication Data

US 2020/0261514 A1    Aug. 20, 2020

Related U.S. Application Data

(60) Provisional application No. 62/799,162, filed on Jan. 31, 2019.

(51) Int. Cl.
| | | |
|---|---|---|
| *A01N 63/00* | (2020.01) | |
| *A61K 35/744* | (2015.01) | |
| *A61K 38/47* | (2006.01) | |
| *A61P 35/00* | (2006.01) | |

(52) U.S. Cl.
CPC ............ *A61K 35/744* (2013.01); *A61K 38/47* (2013.01); *A61P 35/00* (2018.01)

(58) Field of Classification Search
None
See application file for complete search history.

(56) References Cited

FOREIGN PATENT DOCUMENTS

CN    104936611 A    9/2015

OTHER PUBLICATIONS

Rafter et al. Bioscience Microflora , vol. 20, No. 1 ,pp. 19-26, 2001 (Year: 2001).*
Sangwan et al Journal of Food Science Technology vol. 52, No. 7, pp. 4206-4215, 2015 (Year: 2015).*
Tooley et al.Cancer Biology and Therapy 5:6 pp. 593-600, 2006. (Year: 2006).*
Vasiljevic et al. Lait 83, pp. 453-467, 2003. (Year: 2003).*
Daniel, S.G., Ball, C.L., Besselsen, D.G., Doetschman, T. and Hurwitz, B.L., 2017. Functional changes in the gut microbiome contribute to transforming growth factor β-deficient colon cancer. Msystems, 2(5), pp. e00065-17.
Denipote, F.G., Trindade, E.B.S.D.M. and Burini, R.C., 2010. Probióticos e prebióticos na atenção primária ao câncer de cólon. Arquivos de Gastroenterologia, 47(1), pp. 93-98.
Golombos, D.M., Ayangbesan, A., O'Malley, P., Lewicki, P., Barlow, L., Barbieri, C.E., Chan, C., DuLong, C., Abu-Ali, G., Huttenhower, C. and Scherr, D.S., 2018. The role of gut microbiome in the pathogenesis of prostate cancer: a prospective, pilot study. Urology, 111, pp. 122-128.
Healy, A.R. and Herzon, S.B., 2017. Molecular basis of gut microbiome-associated colorectal cancer: a synthetic perspective. Journal of the American Chemical Society, 139(42), pp. 14817-14824.
Liong, M.T., 2008. Roles of probiotics and prebiotics in colon cancer prevention: postulated mechanisms and in-vivo evidence. International journal of molecular sciences, 9(5), pp. 854-863.
Ohara, T., Yoshino, K. and Kitajima, M., 2009. Pre-and probiotics increase host-cell immunological competence, improve bowel movement, and prevent the onset of colon cancer—an analysis based on movements of intestinal microbiota. Rinsho byori. The Japanese journal of clinical pathology, 57(6), pp. 533-541.
Purcell, R.V., Visnovska, M., Biggs, p. J., Schmeier, S. and Frizelle, F.A., 2017. Distinct gut microbiome patterns associate with consensus molecular subtypes of colorectal cancer. Scientific reports, 7(1), pp. 1-12.
Roller, M., Clune, Y., Collins, K., Rechkemmer, G. and Watzl, B., 2007. Consumption of prebiotic inulin enriched with oligofructose in combination with the probiotics Lactobacillus rhamnosus and Bifidobacterium lactis has minor effects on selected immune parameters in polypectomised and colon cancer patients. British Journal of Nutrition, 97(4), pp. 676-684.
Siegel, R.L., Miller, K.D., Fedewa, S.A., Ahnen, D.J., Meester, R.G., Barzi, A. and Jemal, A., 2017. Colorectal cancer statistics, 2017. CA: a cancer journal for clinicians, 67(3), pp. 177-193.
Siegel, R.L. and Miller, K.D., 2017. Jemal ACancer statistics, 2017. Ca Cancer J Clin, 67(1), pp. 7-30.
Vogtmann, E., Hua, X., Zeller, G., Sunagawa, S., Voigt, A.Y., Hercog, R., Goedert, J.J., Shi, J., Bork, P. and Sinha, R., 2016. Colorectal cancer and the human gut microbiome: reproducibility with whole-genome shotgun sequencing. PloS one, 11(5).
Li, et al., "Streptococcus thermophilus Inhibits Colorectal Tumorigenesis Through Secreting β-Galactosidase," Gastroenterology, vol. 160(4), pp. 1179-1193 (Mar. 2021).
Wollowski, et al., "Bacteria Used for the Production of Yogurt Inactivate Carcinogens and Prevent DNA damage in the Colon of Rats.," J Nutr., vol. 129(1), pp. 77-82. (Jan. 1999).

* cited by examiner

*Primary Examiner* — Jana A Hines
*Assistant Examiner* — Khatol S Shahnan Shah
(74) *Attorney, Agent, or Firm* — Kilpatrick Townsend & Stockton LLP

(57) ABSTRACT

The present invention provides novel methods for treating and preventing colorectal cancer in a subject by administering a composition comprising β-galactosidase, a bacterial culture capable of producing β-galactosidase, such as an *S. thermophilus* culture, or a fraction of the culture comprising β-galactosidase. A kit useful for such methods is also provided. In addition, the present invention provides a composition for treating or preventing colon cancer.

13 Claims, 20 Drawing Sheets

Bacteria conditioned-medium dose (%)

THERAPEUTIC AND PROPHYLACTIC TREATMENT FOR COLORECTAL CANCER

RELATED APPLICATIONS

This application claims priority to U.S. Provisional Patent Application No. 62/799,162, filed Jan. 31, 2019, the contents of which are hereby incorporated by reference in the entirety for all purposes.

BACKGROUND OF THE INVENTION

Colorectal cancer (CRC) is the third most common cancer and the fourth leading cause of cancer death globally, with an estimated incidence of 1 million new cases and a mortality of >500 000 deaths per year. According to the data published by the Cancer Registry of the Hong Kong Hospital Authority, CRC constitutes 16.4% of all new cancer cases and 14.3% of all cancer deaths in Hong Kong in 2012.

Several intrinsic (e.g., age, male gender, diabetes mellitus, obesity and inflammatory bowel disease) and extrinsic (e.g., cigarette smoking, inadequate intake of fiber, high consumption of alcohol, red meat and high-fat diet) factors are associated with increased risks for CRC. The epidemiology of CRC is under dynamic changes owing to the changing prevalence and distribution of risk factors. In this regard, CRC incidence in many developing countries, including Asian countries, has increased 2- to 4-fold over the last two decades and has now reached an alarming rate, with Westernization of diet playing a pivotal role.

It has been verified about 100 trillion bacteria exist the in human intestine and, because of their symbiotic and co-operative relationship with the human body, they have a close association with CRC. The association of CRC with altered gut microbiota has been studied in different populations, identifying bacteria such as *Fusobacterium nucleatum* and *Bacteroides fragilis* that may be important in tumorigenesis. In this regard, *F. nucleatum* was found to modify the tumor immune microenvironment which in turn promoted colorectal carcinogenesis. *B. fragilis* also plays an important oncogenic role by producing genotoxins to damage DNA in host cells. *Prevotella* was reported to be enriched in proximal colon cancer and associated with interleukin (IL)-17-producing cells. *Porphyromonas* was also reported to be associated with CRC in different populations.

Several treatment modalities including surgery, chemotherapy, radiation therapy and targeted therapy (e.g., cetuximab and bevacizumab) have been devised to manage CRC. However, the prognosis of patients with metastatic CRC remains dismal, highlighting the importance of prevention of this disease. The long, stepwise progression of CRC from cellular transformation to full-blown metastatic lesions has enabled its prevention through natural compounds or drugs to block or reverse the process. In particular, economic analysis suggests that chemoprevention could be a cost-effective intervention when targeted at intermediate-risk populations following polypectomy. To this end, non-steroidal anti-inflammatory drugs (NSAIDs) and cyclooxygenase-2 (COX-2) inhibitors have been shown to reduce the occurrence of CRC or its precancerous lesions in high-risk individuals. However, the long-term use of these agents has been associated with an increased risk of cardiovascular events, posing the concern of high risk benefit ratio for recommending these agents for CRC chemoprevention. The chemopreventive effects of other agents including folic acid, calcium, vitamin D, and antioxidants have also been explored but their efficacies remain to be established. Probiotics are commensal living microorganisms in the human gut. This invention provides a specific probiotic and its secreted molecules for use in CRC prevention and treatment.

The long, stepwise progression of CRC from cellular transformation to full-blown metastatic lesions has enabled its prevention through natural compounds or drugs to block or reverse the process. However, when targeted at intermediate-risk populations following polypectomy, chemoprevention could be a cost-effective intervention. It has been verified that microbiota have a close association with CRC. To this end, the potential use of bacteria specifically depleted in CRC seems an ideal approach to prevent CRC development. The present inventors discovered for the first time that *S. thermophilus* and its secreted molecules can suppress the growth of CRC in vitro and in vivo. This discovery thus provides important means for the prevention and treatment of CRC.

BRIEF SUMMARY OF THE INVENTION

The present inventors have discovered that the bacterium *S. thermophilus* and its secreted compound(s), such as β-galactosidase, as well as other bacteria capable of secreting β-galactosidase, can effectively suppress the proliferation and viability of human colorectal cancer (CRC) cells and therefore can be used as therapeutic agents for the prevention and treatment of CRC in both prophylactic and therapeutic applications.

As such, in the first aspect, the present invention provides a method for inhibiting cancer cell proliferation. The method includes the step of contacting cancer cells with a composition comprising an effective amount of live *S. thermophilus* or an extract of a *S. thermophilus* culture, β-galactosidase or another β-galactosidase-secreting bacterium or its culture. In some embodiments, the cancer cells are colon cancer cells. In some embodiments, the cancer cells, especially colon cancer cells, are within a subject's body. In some embodiments, the subject has a family history of cancer (such as colon cancer) but has not been diagnosed with cancer. In other embodiments, the subject has been diagnosed with cancer, such as colon cancer. In some embodiments, the composition used in the claimed method is a culture of *S. thermophilus* or another β-galactosidase-secreting bacterium, an extract of such a bacterial (e.g., *S. thermophilus*) culture essentially free of the bacterium (e.g., *S. thermophilus*), an extract of such a bacterial (e.g., *S. thermophilus*) culture essentially free of the bacterium (e.g., *S. thermophilus*) and retained on a membrane with a molecular weight cut-off (MWCO) of 100 kDa following filtration, or an extract of such a bacterial (e.g., *S. thermophilus*) culture comprising β-galactosidase, or β-galactosidase, which may be recombinant in nature or may be isolated from a culture of any bacterium capable of secreting β-galactosidase. In some embodiments, the subject is orally administered a composition comprising an effective amount of β-galactosidase, a live β-galactosidase-secreting bacterium (such as *S. thermophilus*), or an extract of a culture of such a bacterium (such as *S. thermophilus*). For example, the composition may be a *S. thermophilus* culture, an extract of a *S. thermophilus* culture essentially free of *S. thermophilus*, an extract of a *S. thermophilus* culture essentially free of *S. thermophilus* and retained on a membrane with a molecular weight cut-off (MWCO) of 100 kDa following filtration, or an extract of a *S. thermophilus* culture comprising β-galactosidase.

In a second aspect, the present invention provides a kit for treating cancer or reducing risk of cancer in a subject. The kit includes these components: (1) a first container containing a first composition comprising an effective amount of β-galactosidase, a live culture of a bacterium capable of secreting β-galactosidase (such as S. thermophilus), or an extract of such a bacterial (such as S. thermophilus) culture; and (2) a second container containing a second composition comprising an effective amount of an anti-cancer therapeutic agent. In some embodiments, the subject has a family history of cancer, especially colon cancer, but has not been diagnosed with cancer. In some embodiments, the subject has been diagnosed with cancer, especially colon cancer. In some embodiments, the first composition is a culture of a β-galactosidase-secreting bacterium (such as S. thermophilus), especially a live culture, an extract of a β-galactosidase-secreting bacterial (e.g., S. thermophilus) culture essentially free of the bacterium (such as S. thermophilus), an extract of such a bacterial (e.g., S. thermophilus) culture essentially free of the bacterium (e.g., S. thermophilus) and retained on a membrane with a molecular weight cut-off (MWCO) of 100 kDa following filtration, or an extract of a bacterial (e.g., S. thermophilus) culture comprising β-galactosidase, or a composition comprising a β-galactosidase either recombinantly produced or isolated/purified/concentrated from a naturally occurring source. In some embodiments, the first composition is formulated for oral administration, for example, the composition may be presented as a food item, a beverage, a food supplement, a tablet, a capsule, a paste/cream, a liquid or semi-liquid composition. In some embodiments, the composition may be formulated for rectal deposit or insertion. Optionally, the kit further comprises an instruction manual.

In a third aspect, the present invention provides a composition for treating cancer or reducing risk of cancer comprising (1) an effective amount of β-galactosidase, a live culture of a β-galactosidase-secreting bacterium (such as S. thermophilus), or an extract of such a bacterial (e.g., S. thermophilus) culture; and (2) an effective amount of an anti-cancer therapeutic agent; and (3) a physiologically acceptable excipient. In some embodiments, the cancer is colon cancer. In some embodiments, the composition may be formulated as a rectal suppository. In some embodiments, the extract is an extract of a β-galactosidase-secreting bacterial (e.g., S. thermophilus) culture essentially free of the bacterium (e.g., S. thermophilus), an extract of such a bacterial (e.g., S. thermophilus) culture essentially free of the bacterium (e.g., S. thermophilus) and retained on a membrane with a molecular weight cut-off (MWCO) of 100 kDa following filtration, or an extract of a β-galactosidase-secreting bacterial (e.g., S. thermophilus) culture comprising β-galactosidase. In some embodiments, the composition is formulated for oral administration and is a food item, a beverage, a food supplement, a tablet, a capsule, a paste/cream, a liquid or semi-liquid composition. In some embodiments, the composition is formulated for rectal suppository.

In a related aspect, the present invention provides use of β-galactosidase, a β-galactosidase-secreting bacterium or its live culture or extract of the culture, such as live S. thermophilus, a S. thermophilus culture, an extract of a S. thermophilus culture as described herein for treating cancer or for reducing cancer risk, especially colon cancer, in subjects that have been diagnosed with the disease or have known increased risk for the disease although have not yet received a diagnosis of the disease.

DEFINITIONS

Figure 1A:
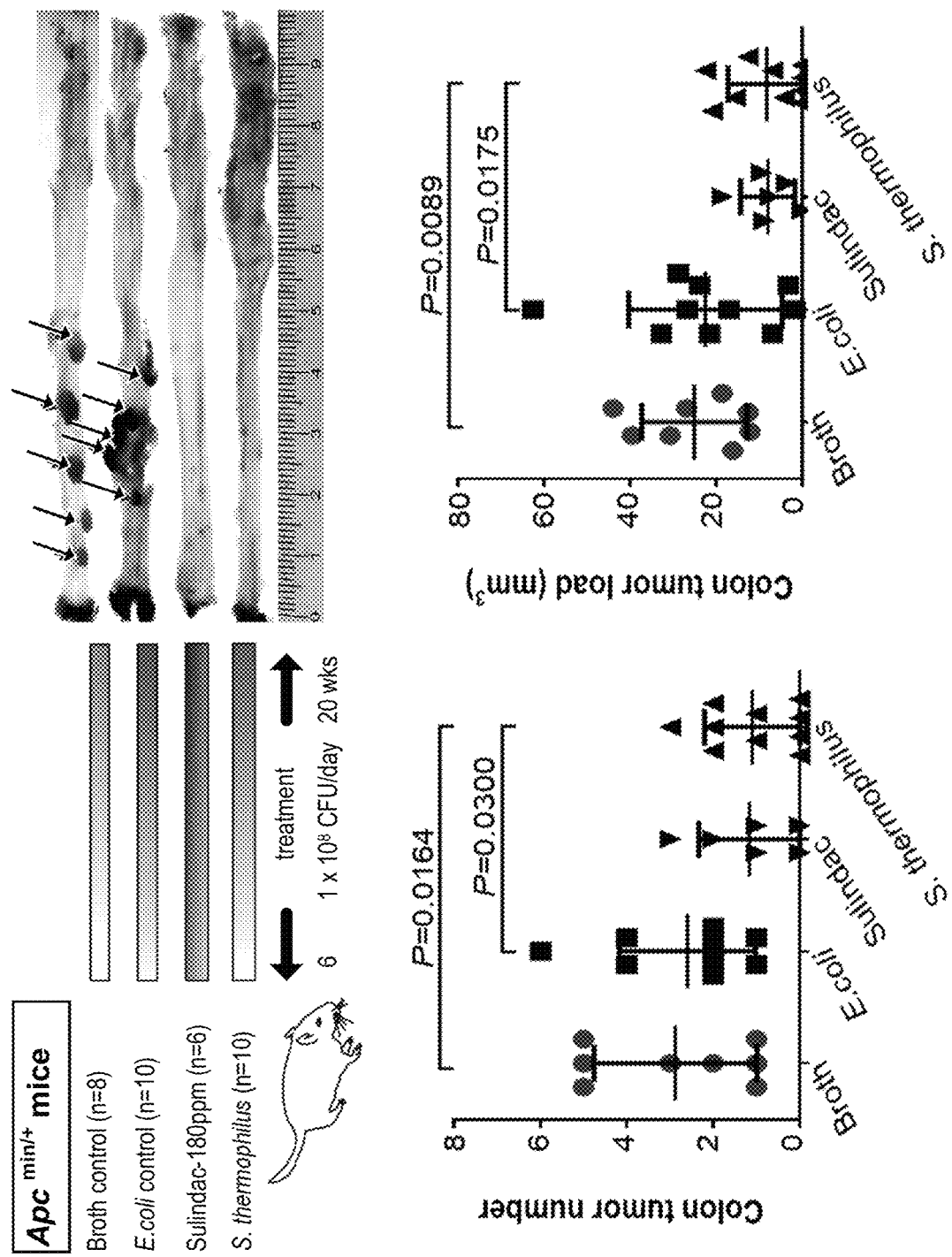
FIGS. 1A-1B shows the prophylactic effect of S. thermophilus on intestinal tumor development in Apc$^{Min/+}$ mice.

In this disclosure the terms "colorectal cancer (CRC)" and "colon cancer" have the same meaning and refer to a cancer of the large intestine (colon), the lower part of human digestive system, although rectal cancer often more specifically refers to a cancer of the last several inches of the colon, the rectum. A "colorectal cancer cell" is a colon epithelial cell possessing characteristics of colon cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, "Streptococcus thermophilus culture" refers to a composition in which the bacteria S. thermophilus are able to proliferate under the suitable conditions including appropriate temperature, ventilation, and moisture etc. Typically, a "Streptococcus thermophilus culture" is an aqueous solution comprising the essential nutrients each in a sufficient quantity for sustaining the growth of S. thermophilus, as well as the bacterium S. thermophilus, and preferably has been placed under conditions suitable for S. thermophilus proliferation for a minimal length of time so as to permit S. thermophilus proliferation, e.g., at least 2, 4, 8, 10 and/or up to 12 hours, thus containing also compounds secreted by S. thermophilus during its life cycle. In this application, "an extract" of a "S. thermophilus culture" refers to any fraction of such a composition or culture having one or more components of the complete S. thermophilus culture removed, for instance, a bacteria-free fraction has all of the bacteria, especially S. thermophilus, removed (e.g., by centrifugation and/or filtration through a membrane such as a 0.22 micron membrane) or inactivated (e.g., by heating, chemical treatment, or irradiation). When the presence of S.

*thermophilus* in a composition (such as an extract of a *S. thermophilus* culture) yields an essentially the same detectable signal as a background signal, a composition is referred to as "essentially free of *S. thermophilus*." Other possible extracts or fractions may include those having compounds within a certain molecular weight range removed or those having only compounds within a certain molecular weight range retained (e.g., by filtration through a membrane of a pre-determined molecular weight cut-off or MWCO and recovering the portion that is retained on the membrane or the portion that passes through the membrane), or those having its protein components digested or otherwise inactivated (e.g., by proteolytic, chemical, or heat treatment).

As used herein, "β-galactosidase" refers to a glycoside hydrolase enzyme that catalyzes the hydrolysis of β-galactosides into monosaccharides through the breaking of a glycosidic bond. The term β-galactosidase includes variants and homologues originated from different bacterial species, such as the β-galactosidase derived from *S. thermophilus*, which are identifiable based on similarity in their amino acid sequences and functional attributes in their enzymatic activities. For example, a "β-galactosidase" as defined herein shares at least 90%, 95%, or higher amino acid sequence identity with the β-galactosidase derived from *S. thermophilus*. A "β-galactosidase" may be naturally occurring or recombinantly produced.

"A β-galactosidase-secreting bacterium" refers to any bacterial species that is capable of producing a detectable level of β-galactosidase, which is released from the bacteria and present in the bacterial culture and detectable by, e.g., at least one immunoassay such as Western Blot. The bacterium may be a naturally occurring one or may be a recombinant one, i.e., genetically engineered or modified. The production and secretion of β-galactosidase by such bacterial cells may be constituent or may be inducible.

As used herein, the term "gene expression" is used to refer to the transcription of a DNA to form an RNA molecule encoding a particular protein or the translation of a protein encoded by a polynucleotide sequence. In other words, both mRNA level and protein level encoded by a gene of interest are encompassed by the term "gene expression level" in this disclosure.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (e.g., β-galactosidase derived from *S. thermophilus*), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in this application, an "increase" or a "decrease" refers to a detectable positive or negative change in quantity from a comparison control, e.g., an established standard control. An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, 1%, or even less variation from the standard control.

The term "inhibiting" or "inhibition," as used herein, refers to any detectable negative effect on a target biological process, such as RNA transcription, protein expression, cell proliferation, cellular signal transduction, cell proliferation, tumorigenicity, metastatic potential, and recurrence of a disease/condition. Typically, an inhibition is reflected in a decrease of at least 10%, 20%, 30%, 40%, or 50% in the target process (e.g., CRC cell proliferation rate) upon application of an inhibitor, when compared to a control where the inhibitor is not applied.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of S. thermophilus culture, or a fraction thereof, especially a fraction comprising the β-galactosidase derived from S. thermophilus, is the amount of said culture or fraction thereof to achieve a decreased level of a target process, e.g., CRC cellular proliferation or viability, such that the risk, symptoms, severity, and/or recurrence change of colon cancer are reduced, reversed, eliminated, prevented, or delayed of the onset in a patient who has been given the S. thermophilus culture or a fraction thereof for therapeutic and/or prophylactic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, colon cancer. Subjects also include individuals currently undergoing therapy that seek manipulation of the therapeutic regimen. Subjects or individuals in need of treatment include those that demonstrate symptoms of colon cancer or are at risk of suffering from colon cancer or its symptoms. For example, a subject in need of treatment includes individuals with a genetic predisposition or risk factors including family history for colon cancer or personal medical history and/or life style choices such as those described in this disclosure that tend to bring about increased risk of the disease, those that have suffered relevant symptoms in the past, those that have been exposed to a triggering substance or event, as well as those suffering from chronic or acute symptoms of the condition. A "subject in need of treatment" may be at any age of life.

DETAILED DESCRIPTION OF THE INVENTION

I. Introduction

Colorectal cancer patients often face a grim prognosis when the disease is detected in its later stages. Early detection and treatment, including prophylactic treatment, of colorectal cancer is therefore critical for improving patient clinical outcome.

The present inventors discovered for the first time that a β-galactosidase-secreting bacterium (such as S. thermophilus) and its secreted compound or compounds (especially β-galactosidase) can provide significant benefits in preventing and treating colorectal cancer (CRC). More specifically, it is revealed by the inventors that the probiotic S. thermophilus and its conditioned-medium (St.CM) containing β-galactosidase can inhibit CRC cell proliferation in vitro and in vivo. Further, it can also induce CRC cell apoptosis and cell cycle arrest. Oral gavage of S. thermophilus to $Apc^{min/+}$ mice and AOM induced CRC mice can slow down the tumor growth and reduce the tumor size significantly. On the other hand, loss of β-galactosidase secretion capability in bacteria leads to abolition of the anti-cancer activities. Overall, this study shows that probiotic bacteria capable of producing β-galactosidase and secreted molecule(s), especially β-galactosidase, can serve as a novel therapeutic agent for treating CRC in both prophylactic and therapeutic applications.

II. Treatment of Colon Cancer

By illustrating the inhibitory effect of β-galactosidase-secreting bacteria such as S. thermophilus and their secreted compound(s), e.g., β-galactosidase, on cancer cells such as colon cancer cells, the present invention provides a novel method for treating patients who have been diagnosed with cancer, e.g., colon cancer, as well as subjects who have not been diagnosed with the disease but are at increased risk of developing the cancer, for example, due to genetic predisposition, family history of cancer (especially colon cancer), and/or personal traits and medical background such as age (50 years or older), gender (male), diabetes mellitus, obesity, and inflammatory bowel disease, as well as smoking and certain dietary choices (e.g., inadequate intake of fiber, high consumption of alcohol, red meat, and high salt/high fat foods). In accordance with this disclosure, a β-galactosidase-producing bacterial culture, such as S. thermophilus culture, or an extract or fraction thereof containing the bacterium and/or its secreted compound(s) (such as β-galactosidase), especially an extract that contains molecules secreted by the bacteria cells with a molecular weight greater than 100 kDa and especially contains β-galactosidase, can be used for administration to such individuals for the purpose to prevent or reduce the risk of the rise of colon cancer among at-risk individuals in prophylactic applications as well as to treat colon cancer patients in therapeutic applications for the purpose to suppress colon cancer cell growth and metastasis, possibly in conjunction with other conventional therapy regiments such as surgical intervention, chemotherapy, radiotherapy, immunotherapy or any combinations thereof.

A. Bacterial Culture and Extracts

A culture of a β-galactosidase-secreting bacterium (which may be a naturally-occurring bacterial species such as S. thermophilus or a recombinant bacterial cell line generated by artificially introducing one or more exogenous genes encoding the enzyme or enhancing the expression of endogenous β-galactosidase) can be established according to methods known in the art and described herein under appropriate conditions. Typically, a live β-galactosidase-secreting bacterial (such as S. thermophilus) culture can be obtained by culturing the bacterium in a liquid medium containing essential nutrients under proper temperature for 12-24 hours so as to permit the bacterial cells to proliferate in the medium. The live bacterial (e.g., S. thermophilus) culture may be directly used for producing a composition in a suitable formula or form for administration to a subject in need thereof. In the alternative, an extract or fraction of such a live culture of a β-galactosidase-secreting bacterium (such as S. thermophilus) may be used instead of the full culture for formulation. For this purpose, a bacteria-free culture extract may be generated from the live culture, e.g., after processing the full culture by centrifugation and/or filtration to remove essentially all of the main bacterial cells (such as S. thermophilus) and other bacteria potentially present from the culture. Also, an extract of the β-galactosidase-secreting bacterial culture (such as an S. thermophilus culture) that is essentially free of the bacterial cells such as S. thermophilus or other bacteria but contains all compounds secreted by the bacterial cells such as S. thermophilus within a preferred molecular weight range may be obtained by a filtration process utilizing a suitable membrane of a desirable pore size. For example, a membrane having a molecular weight cut-off of 100 kDa can be used in filtration, which leaves compounds over the molecular weight retained on the membrane (the retentate portion) while allowing compounds under the molecular weight passing through the membrane (the filtrate portion). Other possible extracts or fractions of a live β-galactosidase-secreting bacterial culture, such as a S. thermophilus culture, may include those that has one particular type of molecules (such as protein) all removed or enriched. For example, one extract may have highly enriched β-galactosidase secreted by a β-galactosidase-secreting bacterium such as S. thermophilus in its culture.

B. β-galactosidase

As shown by the present inventors, β-galactosidase is the compound essential for the anti-cancer activity a β-galactosidase-secreting bacterium is able to support. Such, one aspect of the present invention is the use of β-galactosidase for therapeutic and prophylactic purposes.

The protein β-galactosidase can be obtained via a variety of means, including but not limited to, recombinant production of β-galactosidase by engineered prokaryotic or eukaryotic cells, isolation/purification or partial isolation/enrichment of a naturally-occurring protein β-galactosidase from a source such as a β-galactosidase-secreting bacterial culture. Thus, not only a naturally-occurring β-galactosidase from any bacterial culture, including its variants or homologs with the same type of enzymatic activity—as a glycoside hydrolase enzyme capable of catalyzing the hydrolysis of β-galactosides into monosaccharides by breaking the glycosidic bond, can be used in the claimed methods and compositions of the present invention, any one of the recombinant forms of β-galactosidase protein can also be used. This includes recombinant β-galactosidase proteins of different forms, which may comprise sequence modifications such as deletions, insertions, or substitutions of one or more amino acid residues or may encompass one or more heterologous peptide sequences (one from a source different from the origin of the β-galactosidase) such as affinity or epitope tags, but which nevertheless retain the same type of enzymatic activity of catalyzing the hydrolysis of β-galactosides.

C. Pharmaceutical Compositions

1. Formulations

β-galactosidase, a live bacterial culture capable of producing β-galactosidase (such as a S. thermophilus culture), or an extract thereof, especially one containing β-galactosidase, is useful in the manufacture of a pharmaceutical composition or a medicament. A pharmaceutical composition or medicament can be administered to a subject for the treatment of colon cancer, especially for prophylaxis.

β-galactosidase, a β-galactosidase-producing bacterial culture such as a S. thermophilus culture, or its extract used in the treatment method of the present invention are useful in the manufacture of a pharmaceutical composition or a medicament or a food item including a beverage or food supplement in conjunction or mixture with one or more physiologically acceptable excipients or carriers suitable for administration.

An exemplary pharmaceutical composition for such therapeutic use comprises (i) an effective amount of β-galactosidase, a live culture of a β-galactosidase-secreting bacterium, such as S. thermophilus culture, or an extract as described herein, and (ii) a pharmaceutically acceptable excipient or carrier. The terms pharmaceutically-acceptable and physiologically-acceptable are used synonymously herein.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally, depending on the anatomic sites for delivery, such as where the cancer is present or likely to arise: for example, colon for colon cancer, stomach for gastric cancer, and skin for skin cancer.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a composition of the present invention with one or more carriers. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament or a food item or a food supplement can take the form of, for example, a tablet or a capsule prepared by conventional means with a pharmaceutically acceptable excipient. Preferred are tablets and gelatin capsules comprising the active ingredient, i.e., β-galactosidase, a β-galactosidase-secreting bacterial culture such as a *S. thermophilus* culture, or an extract thereof especially containing β-galactosidase, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound. For use in food items, the composition or active ingredient (e.g., β-galactosidase, bacterial cells capable of producing β-galactosidase, a live culture thereof, or an extract thereof containing β-galactosidase) of this invention may be directly added to conventional food items such as a supplement or may be mixed into a beverage or snack.

Active compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient (e.g., β-galactosidase, bacterial cells capable of producing β-galactosidase, a live culture thereof, or an extract thereof containing β-galactosidase) can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, or about 5 to 25%, of the composition or active ingredients derived from a β-galactosidase-producing bacterial culture such as *S. thermophilus* culture, e.g., β-galactosidase.

For administration by inhalation, the composition or active ingredients derived from the β-galactosidase-producing bacterial culture such as an *S. thermophilus* culture (e.g., β-galactosidase) may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds or active ingredients of this invention can also be formulated in rectal compositions, for example, suppositories or retention enemas, for example, containing conventional suppository bases, for example, cocoa butter or other glycerides.

Furthermore, the compounds or active ingredients can be formulated as a depot preparation. Such long-acting formulations can be administered by implantation (for example, subcutaneously or intramuscularly) or by intramuscular injection. Thus, for example, the compounds or active ingredients can be formulated with suitable polymeric or hydrophobic materials (for example as an emulsion in an acceptable oil) or ion exchange resins, or as sparingly soluble derivatives, for example, as a sparingly soluble salt.

In some cases, a pharmaceutical composition or medicament of the present invention comprises (i) an effective amount of a composition as described herein that suppresses the proliferation or promotes the death of cancer cells especially colon cancer cells, and (ii) another therapeutic agent especially a known anti-cancer drug such as a chemotherapeutic agent against cancer including colon cancer. When used with a composition or active ingredient of the present invention, such therapeutic agent may be used individually, sequentially, or in combination with one or more other such therapeutic agents (e.g., a first therapeutic agent, a second therapeutic agent, and a composition of the present invention). Administration may be by the same or different route of administration or together in the same pharmaceutical formulation.

III. Compositions and Kits

The invention provides compositions and kits for practicing the methods described herein to treat cancer or to reduce the risk of cancer development, especially colon cancer, in a subject. For example, a composition useful for the therapeutic or prophylactic applications typically contains (1) an effective amount of β-galactosidase, a live β-galactosidase-secreting bacterium such as *S. thermophilus*, a β-galactosidase-secreting bacterial culture such as a *S. thermophilus* culture, or an extract of such culture, especially containing β-galactosidase; and (2) a carrier or excipient, especially one that is appropriate for formulation suitable for oral administration. For example, one extract of such a bacterial culture such as an *S. thermophilus* culture is an extract that is essentially free of the bacterial cells (e.g., *S. thermophilus* and/or other bacterial cells) but retains compounds secreted by the β-galactosidase-secreting bacterium (e.g., *S. thermophilus*) with a molecular weight greater than 100 kDa, including β-galactosidase. In some cases the composition will be formulated for oral administration or rectal suppository. Optionally the composition will further comprise a second therapeutically effective agent, such as a chemotherapeutic agent known to be effective for cancer treatment.

Kits for carrying out the treatment methods of the present invention typically include (1) a first container containing a composition of this invention, e.g., one comprising an effective amount of β-galactosidase, a live β-galactosidase-secreting bacterium such as *S. thermophilus*, a β-galactosidase-secreting bacterial culture such as *S. thermophilus* culture, or an extract of such culture, for example, an extract that is essentially free of bacteria (e.g., *S. thermophilus* and/or other bacterial cells) but retains compounds secreted by *S. thermophilus* with a molecular weight greater than 100 kDa, including β-galactosidase; and (2) a second container containing an effective amount of a second therapeutically effective agent, such as a chemotherapeutic agent known to be effective for cancer treatment. Kits may further include an instruction manual to guide users for properly dispensing the compositions.

EXAMPLES

The following examples are provided by way of illustration only and not by way of limitation. Those of skill in the art will readily recognize a variety of non-critical parameters that could be changed or modified to yield essentially the same or similar results.

Example 1: *S. thermophilus* and its Inhibitory Effect on CRC

Introduction

The present inventors have identified *S. thermophilus* and its secreted molecules as novel prophylactics or therapeutics for the prevention or treatment of CRC. More specifically, the inventors show that, coculturing *S. thermophilus* with colon cells can inhibit cancer cell proliferation in vitro and in vivo. Compounds secreted by the bacteria can also have the same effect in vitro and in vivo. Moreover, the secreted molecules can induce programmed cell death and cause cell cycle arrest at G0/G1 phase. The administration of this specific probiotics can prevent CRC formation in animals. Therefore, *S. thermophilus* and its secreted molecules are useful for the prevention and treatment of CRC.

Materials and Methods
Bacterial Strain and Culture Condition

*Streptococcus thermophilus* [ATCC 19258] was purchased from the American Tissue Culture Collection (Manassas, Va.) and cultured in Brain Heart Infusion (BHI) Broth (CM1135B; Thermo Fisher Scientific, West Palm Beach, Fla.) for 24 hours at 37° C. in aerobic condition. A nonpathogenic human commensal intestinal bacteria, *Escherichia coli* strain MG1655 was used as a control and was cultured in the same condition as *S. thermophilus*. The mutant *S. thermophilus* (LacZ knockout) was constructed by homologous recombination and were cultured in selective antibiotic (50 ug/ml kanamycin) BHI broth.

Cell Culture

CRC cell lines HCT116, HT29 and Caco-2 were obtained from the American Type Culture Collection. Human normal colon epithelial cell line NCM460 was obtained from INCELL Corporation (San Antonio, Tex.). All the cell lines were growth in high-glucose Dulbecco's Modified Eagle's Medium (DMEM) (Gibco BRL, Grand Island, N.Y.) supplemented with 10% (vol/vol) fetal bovine serum (FBS), 1% penicillin/streptomycin in a humidified atmosphere containing 5% $CO_2$.

Preparation of the Conditioned Medium

When the density of bacteria reached at OD=0.5 at A600 nm, the bacteria culture medium will be centrifuged (1,000×g for 15 min) and filtered through a 0.2-μm pore-size filter to obtain the conditioned-medium.

The Isolation of the Anti-Tumor Molecule

The prepared conditioned-medium was separated with a molecular weight cutoff spin column (Merck KGaA, Darmstadt, Germany). The >100 KDa fraction was obtained by centrifuge the conditioned-medium through a 100,000 NMWL membrane.

Characterization of the Anti-Tumor Molecules

The anti-tumor molecules were digested by protease K at 55° C. for 2 h or were heat-inactivated at 100° C. for 30 min. The protease K was then inactivated at 95° C. for 10 min.

Silver Stain for Mass Spectrometry

The anti-tumor molecule was separated by sodium dodecyl sulfate polyacrylamide gel electrophoresis (5%) (SDS-PAGE). The silver stain was performed following the instructions provided by the manufacture (Thermo Scientific, Rockford, USA). After staining, the >100 KDa fraction bands were removed and in-gel digestion was performed. The obtained supernatant was subjected to MS analysis.

Mass Spectrometry

The fraction was diluted in methanol and injected into a Nano Frontier eID Liquid Chromatography Mass Spectrometer (Hitachi High-technologies, Japan) at 3 μl/min. The detected signal was analyzed according the existed database.

Colony Formation Assay

Colon cells (1000 per well) were seeded on six-well plates, following the treatment of St.CM (1% St.CM in DMEM). Brain heart infusion (BHI) and the conditioned-medium of *E. coli* (Ec.CM) were used as control. The treatment medium was changed every 3 days. After culturing for 14-18 days, cells were fixed with 70% ethanol and stained with 0.5% crystal violet solution. Colony with more than 50 cells was counted. All experiments were performed three times in triplicate.

Cell Viability Assay

Cell viability was determined by the 3-(4,5-dimethylthiazol-2-yl)-2,5-diphenyltetrazolium (MTT) assay. For each well in the 96-well plate, 1,000 cells were seeded and treated with 1% vol/vol of bacteria conditioned medium or bacteria directly. After 24, 48 and 72 hr, 10 μL MTT (5 mg/ml) reagent was added into the culture medium, respectively. The cells were then incubated at 37° C. until the intracellular purple formazan crystals are visible, which were then dissolved by DMSO. Absorbance of the samples was measured at 570 nm.

Flow Cytometry

For cell cycle analysis, the treated cells were fixed by 70% ethanol overnight. Cells were then stained with 50 μg/mL propidium iodide (PI) (BD Pharmingen, San Jose, Calif., USA) for 30 minutes at 4° C. in dark. 10,000 cells were counted by FACSAria cell sorter (BD Biosciences, Franklin Lakes, N.J., USA) and cell-cycle profiles were analyzed by ModFit 3.0 software (Verity Software House, Topsham, Me., USA). The proportion of apoptotic cells was evaluated using Annexin V apoptosis assay. The treated cells were collected and resuspended in 100 μL annexin-binding buffer (10 mM HEPES, 140 mM NaCl and 2.5 mM $CaCl_2$, pH 7.4) containing 5 μL Annexin V conjugated with Allophycocyanin and 50 μg/mL PI (BD Pharmingen). After incubation for 15 min at room temperature, cells were mixed with additional 400 µL of ice-cold annexin-binding buffer and analyzed using FACSAria cell sorter (BD Biosciences).

Ki-67 Staining

Cell proliferation was assayed by immunoperoxidase staining with anti-Ki-67 antibody (ab833; Abcam, Cambridge, UK). Negative controls were run by replacing the primary antibody with nonimmune serum. The proliferation index was determined by counting the numbers of positive staining cells as percentages of the total number of tumor cells. At least 1000 tumor cells were counted each time.

Western Blotting Analysis

Total protein was isolated and separated by sodium dodecyl sulfate polyacrylamide gel electrophoresis (6%-12%) (SDS-PAGE). The protein in SDS-PAGE were then transferred onto polyvinylidene difluoride (PVDF) membranes (EMD Millipore, Billerica, Mass., USA) for about 1-2 hours, which was then blocked with 10% non-fat milk in 0.05% Tris-based saline-Tween 20 for 2 hours at RT. The membrane was incubated with primary antibodies overnight at 4° C. and then with secondary antibody at RT for 1 hour. The protein band intensities were detected by ECL Plus Western blotting Detection Reagents (GE Healthcare).

Histopathology

At the end of animal experiment, the fresh tissues were flattened on filter paper and fixed overnight in 10% buffered formalin for histopathological assessment. Sections of 5 µm were stained with H&E for histologic diagnosis by an experienced pathologist. Dysplasia was determined following the latest World Health Organization's Classification of TuMORS OF THE Digestive System.

In Vivo Tumorigenicity—Xenograft Tumor Model

HCT116 (1×106 cells in 0.1 ml phosphate-buffered saline) were injected subcutaneously into the right dorsal flank of four 4-week-old male Balb/c nude mice, separately (6/group). Intro-tumoral injection of the conditioned-medium was performed 3 times/week. Tumor diameter was measured every 2 days. Tumor volume ($mm^3$) was estimated by measuring the longest and shortest diameter of the tumor and calculating as follows: volume=(shortest diameter)2× (longest diameter)×0.5. After 19 days, the mice were sacrificed, and the tumors were weighed and fixed in formalin for histological analysis. All experimental procedures were approved by the Animal Ethics Committee of the Chinese University of Hong Kong.

In Vivo Tumorigenicity—Colitis-Associated Cancer Model 6-week-old male conventional C57BL/6 wild-type mice were subjected 6 consecutive injection of AOM (10 mg/kg, intraperitoneal injection) at 1-week intervals, followed by the presence or absence of an antibiotic cocktail (0.1 g/L of Vancomycin, 0.1 g/L of Neomycin, 0.1 g/L of Penicillin and 0.2 g/L of Metronidazole) in drinking water for 2 weeks. The mice were then gavaged with 1×108 CFU of *S. thermophilus*, *E. coli* MG1655 or the same volume of PBS every day for 20 weeks for the development of neoplastic lesions. Sulindac (180 ppm/week) was used as a positive control.

In Vivo Tumorigenicity—$APC^{Min/+}$ Model

C57BL/6J-ApcMin/J mice, which harbor germline mutation in the tumor suppressor gene APC and develop intestinal polyps spontaneously, have been purchased from the Jackson Laboratory (Bar Harbor, Me., USA) and are currently maintained in the animal facility at our University. Genotyping will be conducted by routine allele-specific PCR assay. The same treatment with AOM model was used in eight-week-old male $APC^{min/+}$ mice and they were raised till 20 weeks for the evaluation of the bacteria treatment efficacy.

Statistical Analysis

Data are expressed as mean±standard deviation (SD) from 3 dependent experiments. The independent Student t test was used to compare the difference between two groups. One-way analysis of variance (ANOVA) was used to compare the difference between multiple groups. Differences with P-value<0.05 were considered statistically significant. All tests were performed using GraphPad Prism, version 6.0.

S. thermophilus Mutant Strain Construction

The mutant *S. thermophilus* (LacZ knockout) was constructed by homologous recombination. Kanamycin resistance gene fragment was amplified from the pCR2.1-TOPO plasmid. Sequences around 1 kb upstream and downstream with 500 bp space were amplified from the genomic DNA of *S. thermophilus*, respectively. Subsequently, three DNA fragments, including the sequences around 1 kb upstream of the LacZ gene encoding β-galactosidase and 900 bp kanamycin resistance gene, and sequences around 1 kb downstream of the LacZ gene, were cleaved by restriction enzymes and then linked successively. The recombinant DNA fragment was linked into the pCR2.1-TOPO plasmid using the T-A cloning technique. The recombinant pCR2.1-TOPO plasmid was transformed into the competent cells of *S. thermophilus* by electroporation (1.8 kV, 200Ω, and 25 µF). The competent cell was constructed by exposing *S. thermophilus* to 50 ml BHI broth containing 20 mM D-L threonine for 2-2.5 hours to reach an optical density (OD) 600 of 0.2-0.3. The cells pellets (4,500×g, 15 minutes) were washed with 5 ml electroporation buffer (7 mM HEPES, 1 mM $MgCl_2$, pH 6.0) and resuspended to an OD600 of 20 in the same buffer to obtain the electrocompetent cells. The electroporated cells were spread onto pre-warmed BHI agar plates containing X-gal and the representative putative transformant colonies were then cultured in selective antibiotic (50 ug/ml kanamycin) for genomic isolation and β-galactosidase activity test. The presence of the relevant plasmid species was confirmed by agarose gel electrophoretic examination and the derivatives were ensured by 16S ribosomal RNA gene sequencing.

Results

Figure 1B:
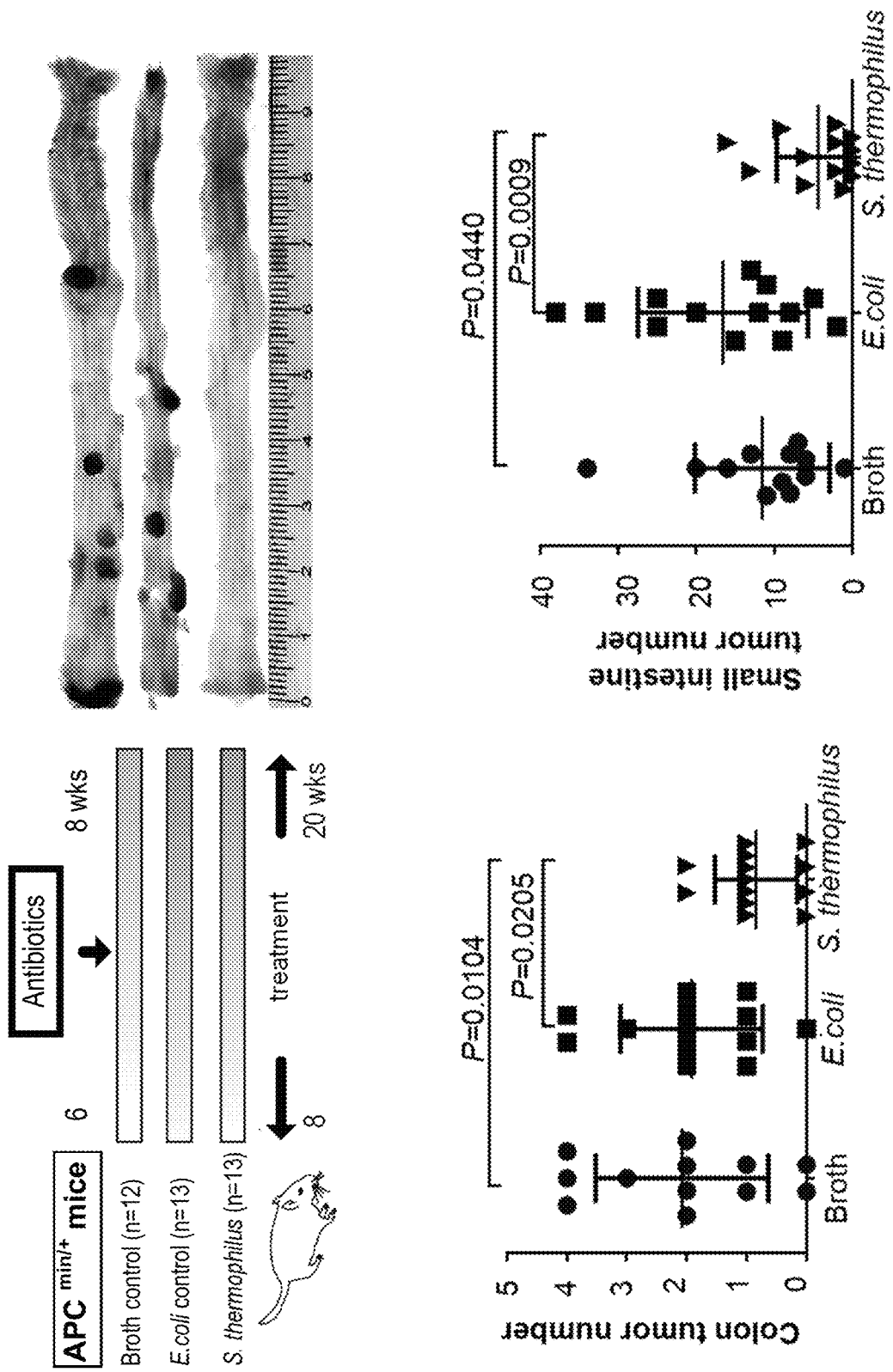

*Streptococcus thermophilus* Reduces Colonic Tumorigenesis in $Apc^{min/+}$ Mice with or without Microbiota Depletion To evaluate whether *S. thermophilus* could have anti-tumorigenic effect in mice. 6 weeks old Non-gut flora-deficiency and gut glora-deficiency $Apc^{min/+}$ mice were gavaged with 1×$10^8$ colony forming units (CFU) of *S. thermophilus* per day for 14 weeks, respectively. At the end of the experiments, the whole intestinal tract of each mouse was carefully harvested for visual examination of macroscopic tumors. It was discovered that *S. thermophilus*-treated mice had a lower tumor number, size (FIG. 1A, FIG. 1B) compared to both the *E. coli* strain MG1655 and the broth control group. Sulindac (180 ppm per 3 days) was used as positive control.

*Streptococcus thermophilus* Reduces AOM-Induced Colonic Tumorigenesis in Mice

Figure 2:
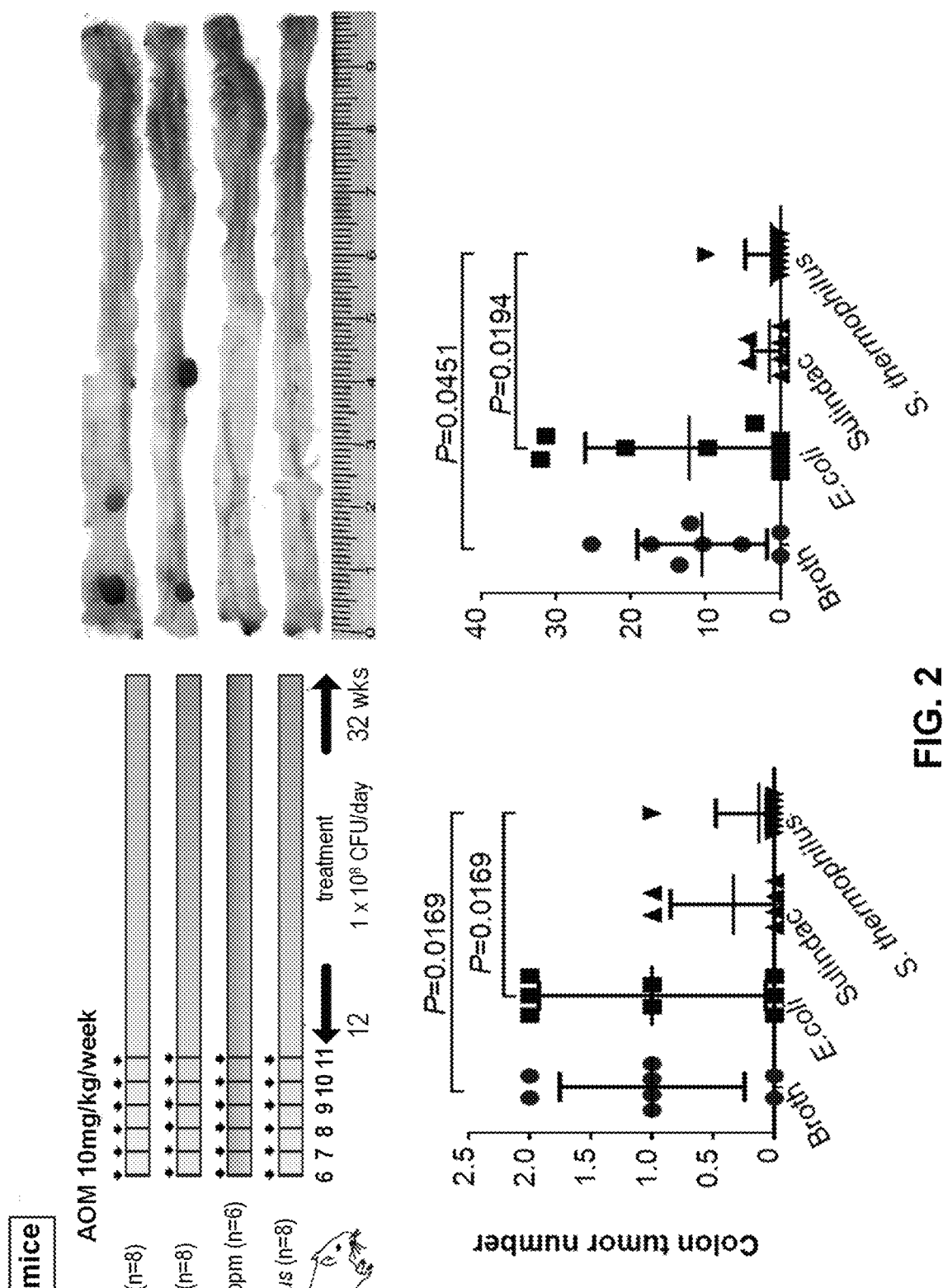
FIG. 2 shows the prophylactic effect of S. thermophilus on intestinal tumor development in carcinogen (AOM)-injected mice.

To further observe whether *S. thermophilus* could reduce tumorigenesis in mice, *S. thermophilus* was gavaged to the mice after 6 times AOM injection for 20 weeks. The whole intestinal tract of each mouse was examined at the end of the experiments. Consistent results were obtained with $Apc^{min/+}$ mice model (FIG. 2).

*Streptococcus thermophilus* Inhibits the Proliferation of Colon Cancer Cells

Figure 3A:
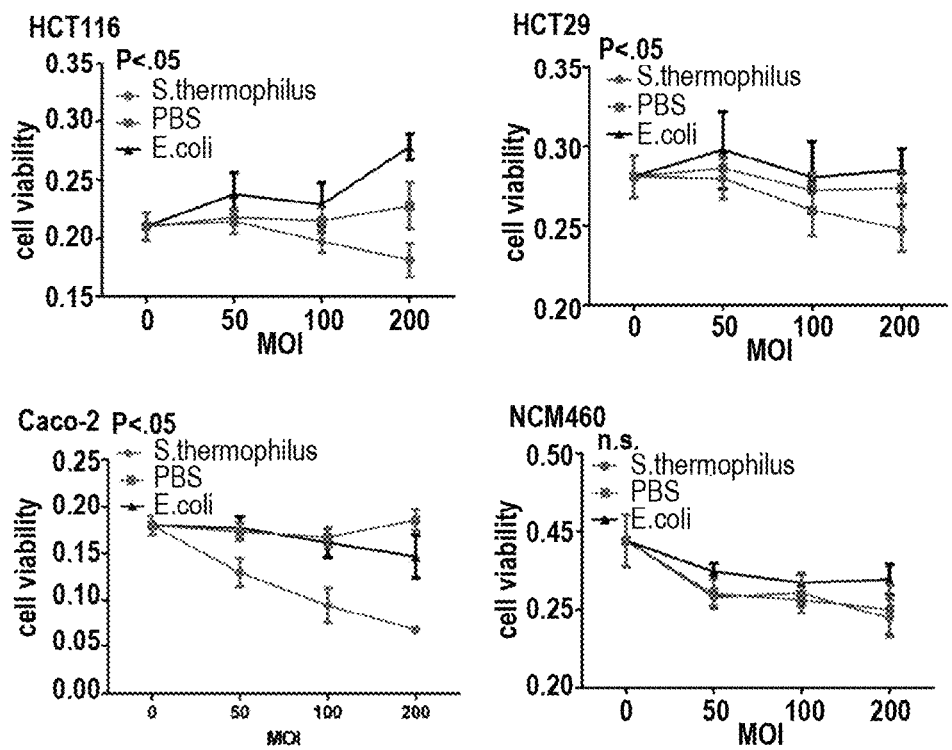
FIG. 3 shows the inhibitory effects of S. thermophilus on the viability of cancerous (HCT116, HT29, Caco-2) and normal (NCM460) colonic epithelial cells.
Figure 3B:
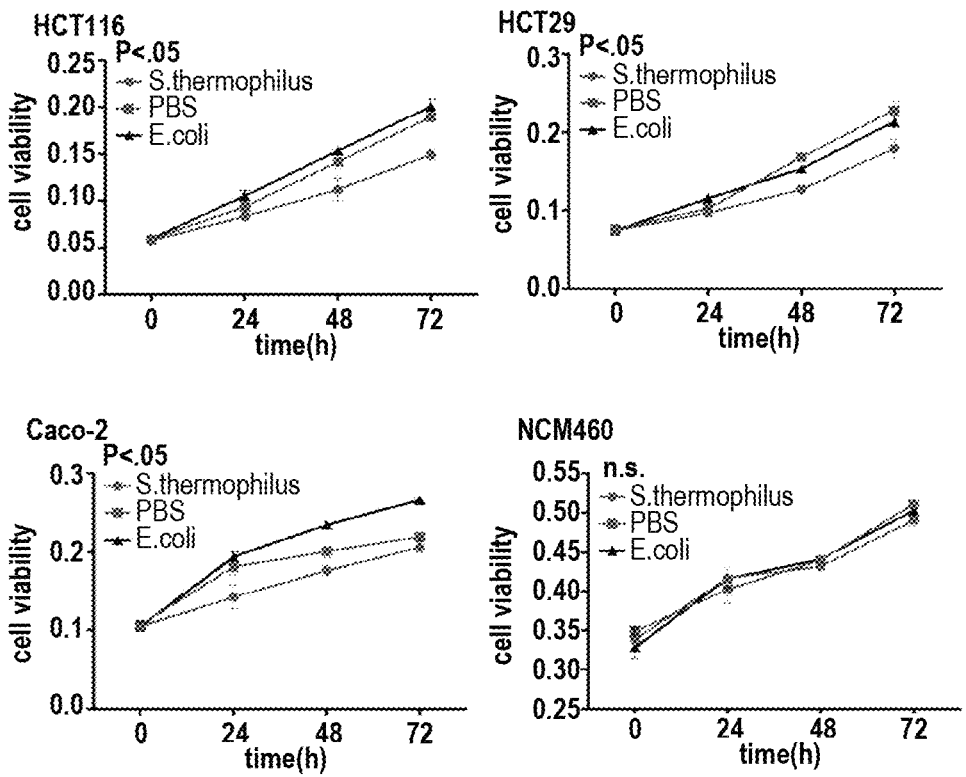

To elucidate the anti-tumorigenic role of *S. thermophilus* on colon cells, MTT was performed to examine the cell viability. Colon cancer cell lines HCT116, HT29 and Caco-2 and colon normal epithelial cell line NCM460 were treated with *S. thermophilus* (multiplicity of infection (MOI)=50, 100, 200) for 4 hours. *E. coli* strain MG1655 and PBS were used as control. As shown in FIG. 3, *S. thermophilus* caused a significant decrease of cell proliferation in colon cancer cell lines in a time- and MOI-dependent manner. However, for the normal epithelial cells, the inhibition effect has no significant difference.

Killed-*Streptococcus thermophilus* has No Effect

Figure 4A:
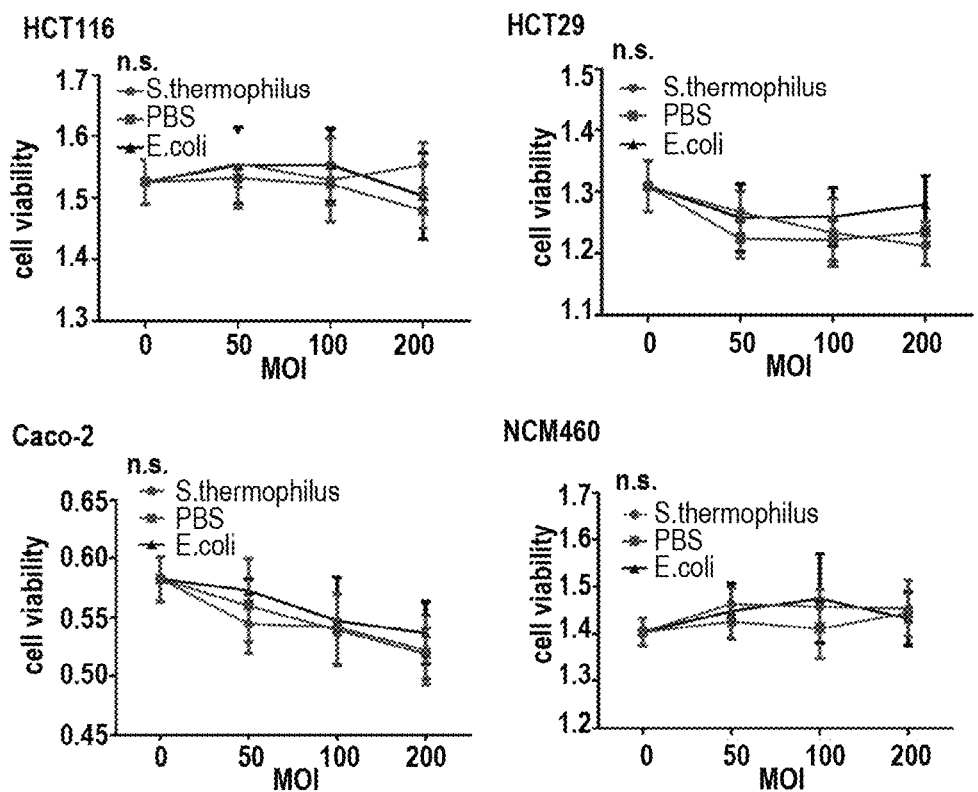
FIG. 4 shows that the killed-S. thermophilus has no effect on CRC cell lines.
Figure 4B:
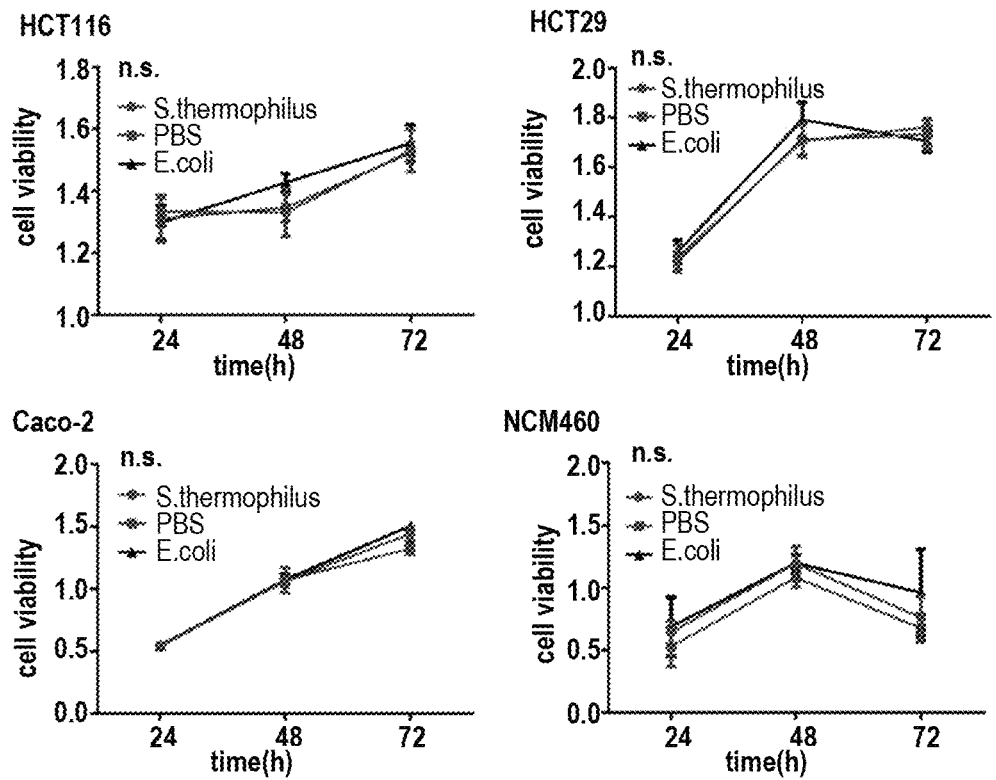

To determine whether the anti-tumor effect was cause by *S. thermophilus* itself or its product, live *S. thermophilus* were killed by autoclaving, and the killed bacteria were then exposed to colon cells. However, no decreased viability of colon cancer cells was observed (FIG. 4), which indicates that the anti-tumor effect requires living *S. thermophilus*.

Figure 5A:
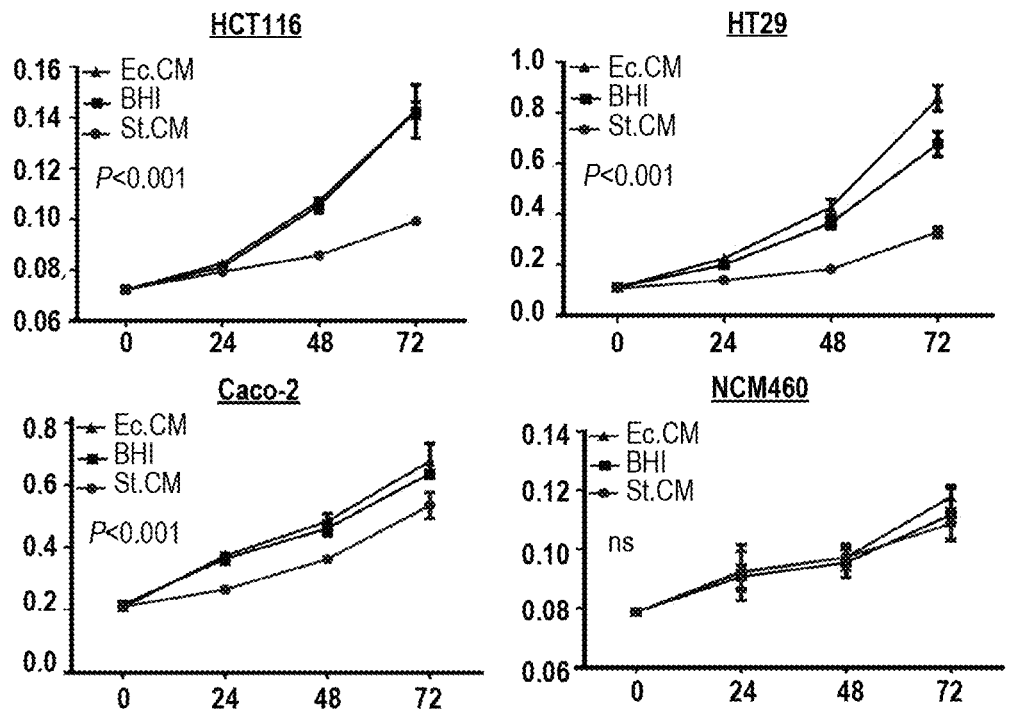
FIGS. 5A-5B shows the time- and concentration-dependent inhibitory effects of St.CM on CRC cell lines.
Figure 5B:
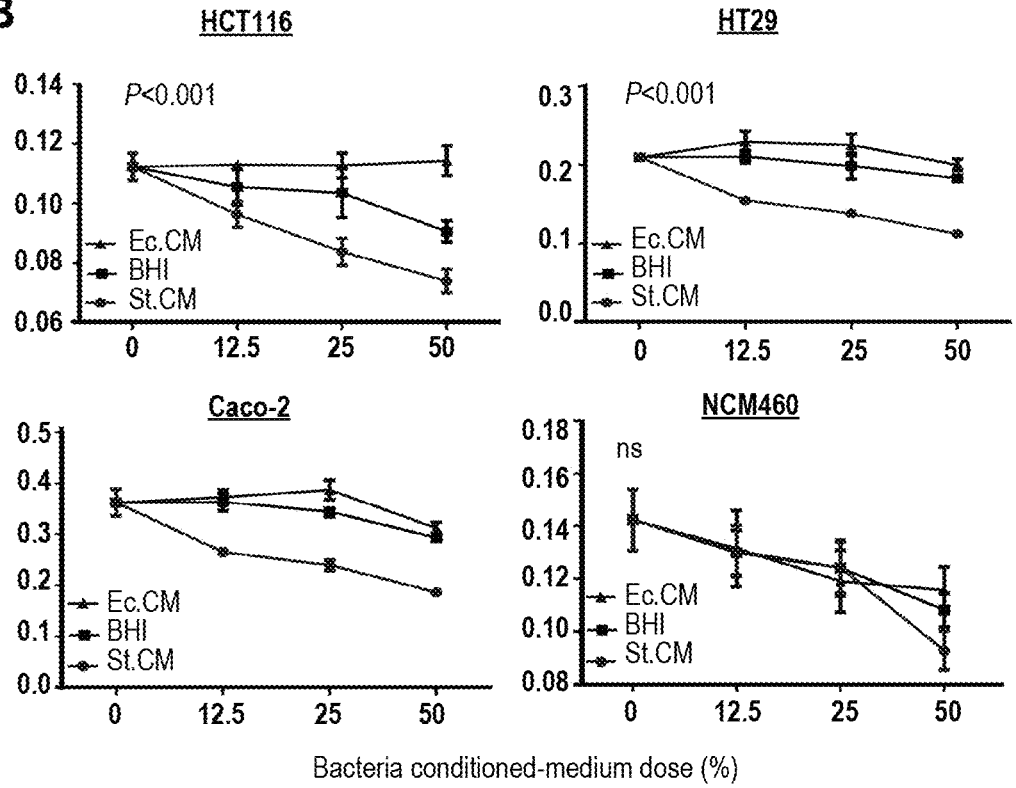

Conditioned-Medium of *Streptococcus thermophilus* (St.CM) Inhibits the Proliferation of Colon Cancer Cells To clarify the anti-tumor effect of the bacterial product, all bacteria bodies and debris in the culture supernatants were removed by centrifugation and filtration using a 0.22-μm membrane to obtain the conditioned-medium. Colon cancer cells, namely HCT116, HT29, Caco-2, and a colon normal epithelial cell line NCM460 were co-cultured with the conditioned-medium at different dosage (12.5, 25, 50%) for 4 consecutive days. MTT assay indicated that St.CM suppressed the proliferation of colon cancer cell in time—(FIG. 5.A) and dose-dependent manner (FIG. 5.B). All these data revealed that the secreted molecules, but not the bacterial body or debris, exhibited the growth-inhibitory effect.

St.CM Promotes the Apoptosis of Colon Cancer Cells

Figure 6:
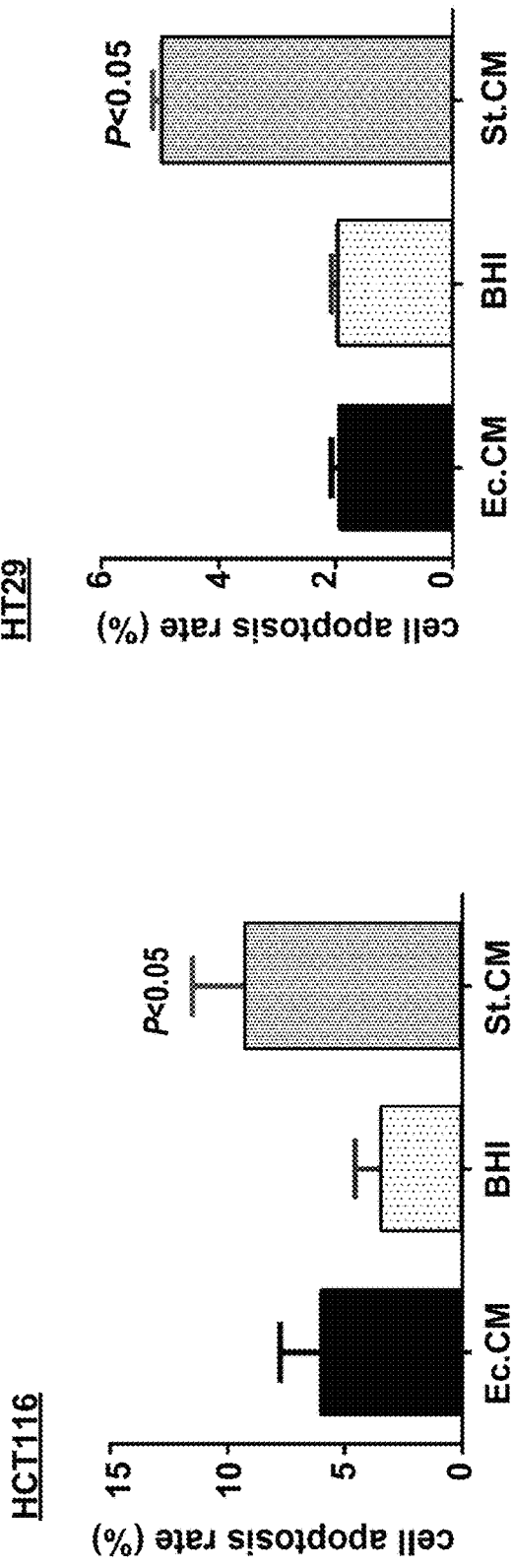
FIG. 6 shows that St.CM induced apoptotic cell death in cancerous (HCT116, HT29, Caco-2) but not normal (NCM460) colonic epithelial cells.
Figure 6:
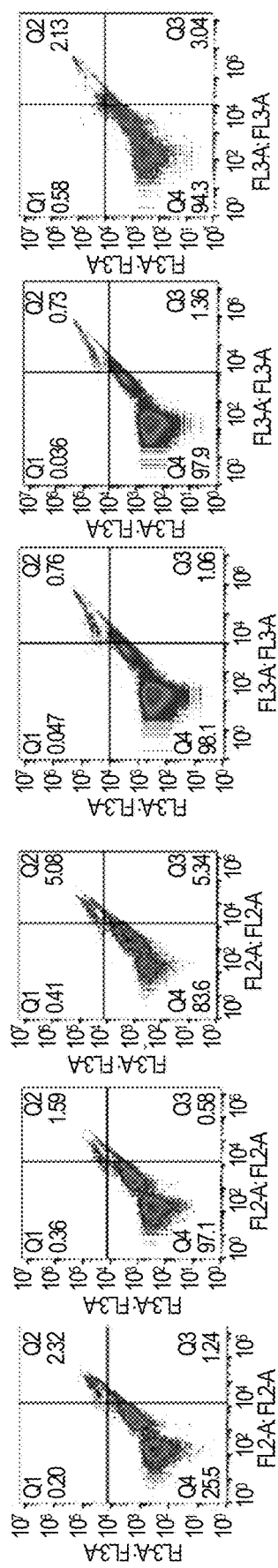
Figure 6:
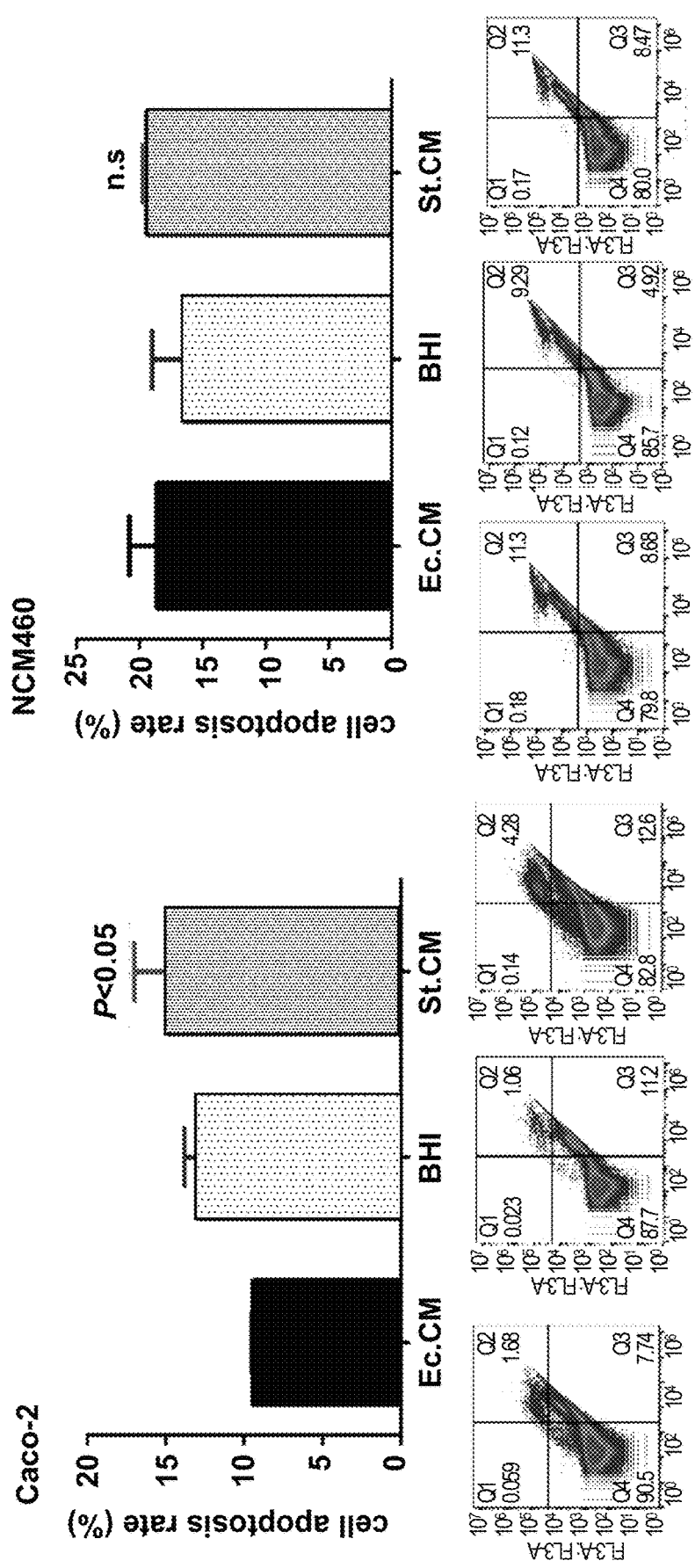

Suppression of viability of tumor cells is usually associated with concomitant activation of cell death pathways. The contribution of apoptosis to the observed growth inhibition of St.CM was examined using flow cytometry with Annexin V and propidium iodide (PI) double staining. The results showed an increase in the numbers of apoptotic cells in St.CM-treated cells compared with BHI or Ec.CM-treated cells (FIG. 6). This effect was also observed in colon normal epithelial cell line NCM460. These findings indicated that the apoptosis induced by St.CM accounts for the anti-tumor effect in colon cancer cells.

Isolation of Tumor-Suppressive Probiotic-Secreted Molecules

To further determine the anti-tumor fraction derived from *S. thermophilus*, the St.CM was separated using 100-KDa molecular weight cutoff (MWCO) membranes. The cells were then exposed to 1% (vol/vol)>100-KDa fraction or <100-KDa fraction for 24 hours, respectively.

St.CM>100-KDa Fraction Inhibits the Viability of Colon Cancer Cells

Figure 7A:
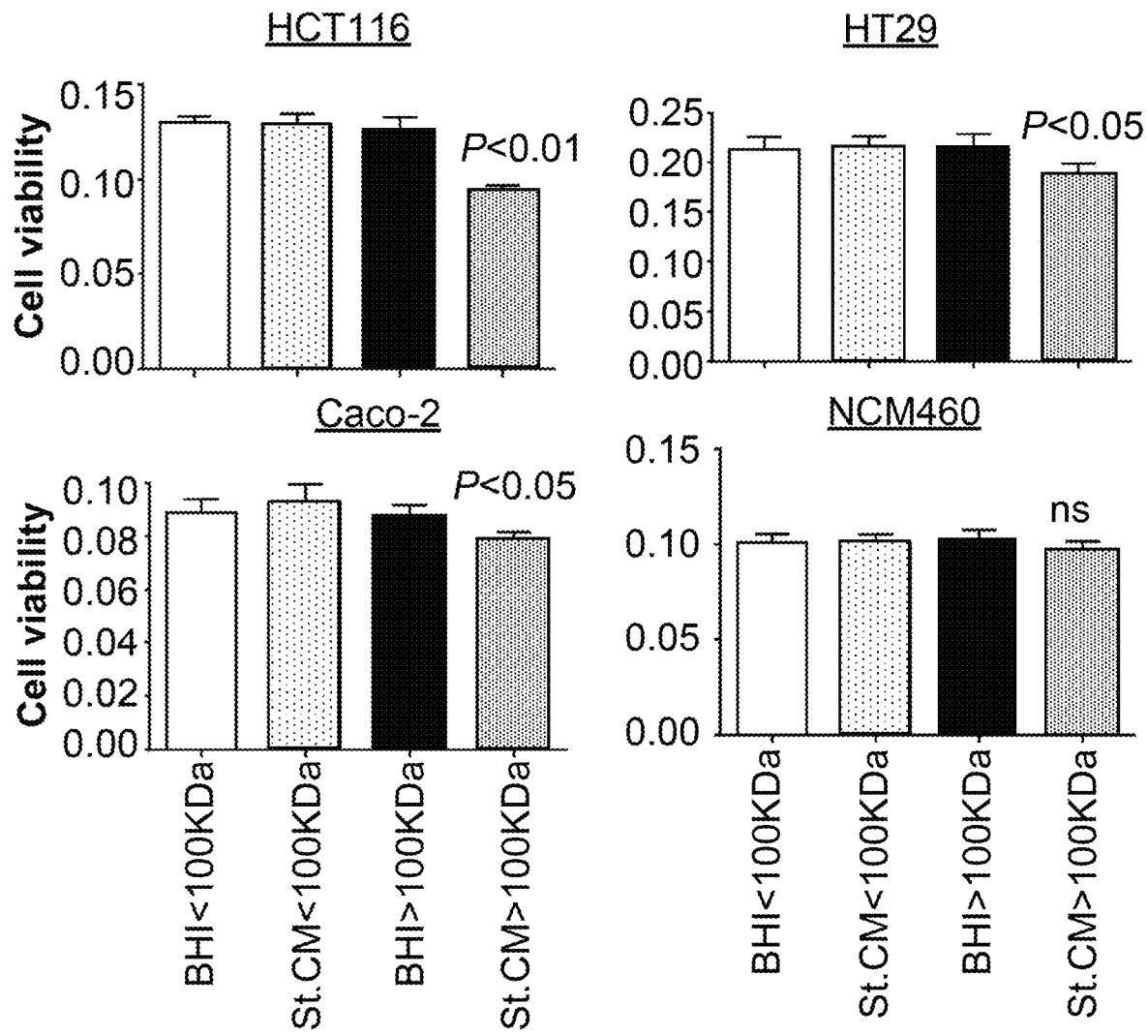
FIGS. 7A-7D shows the tumor-suppressive effect of >100 KDa fraction from St.CM.
Figure 7B:
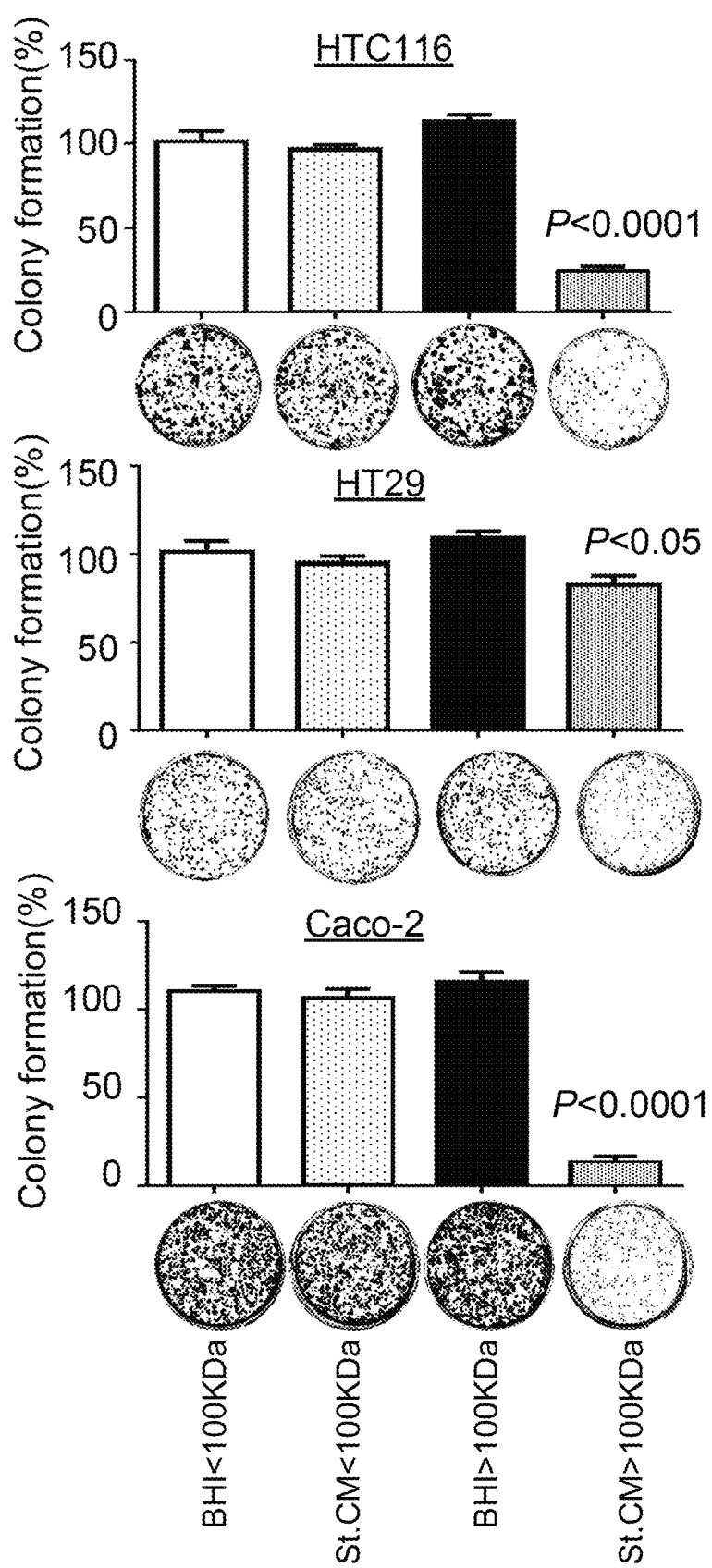
Figure 7C:
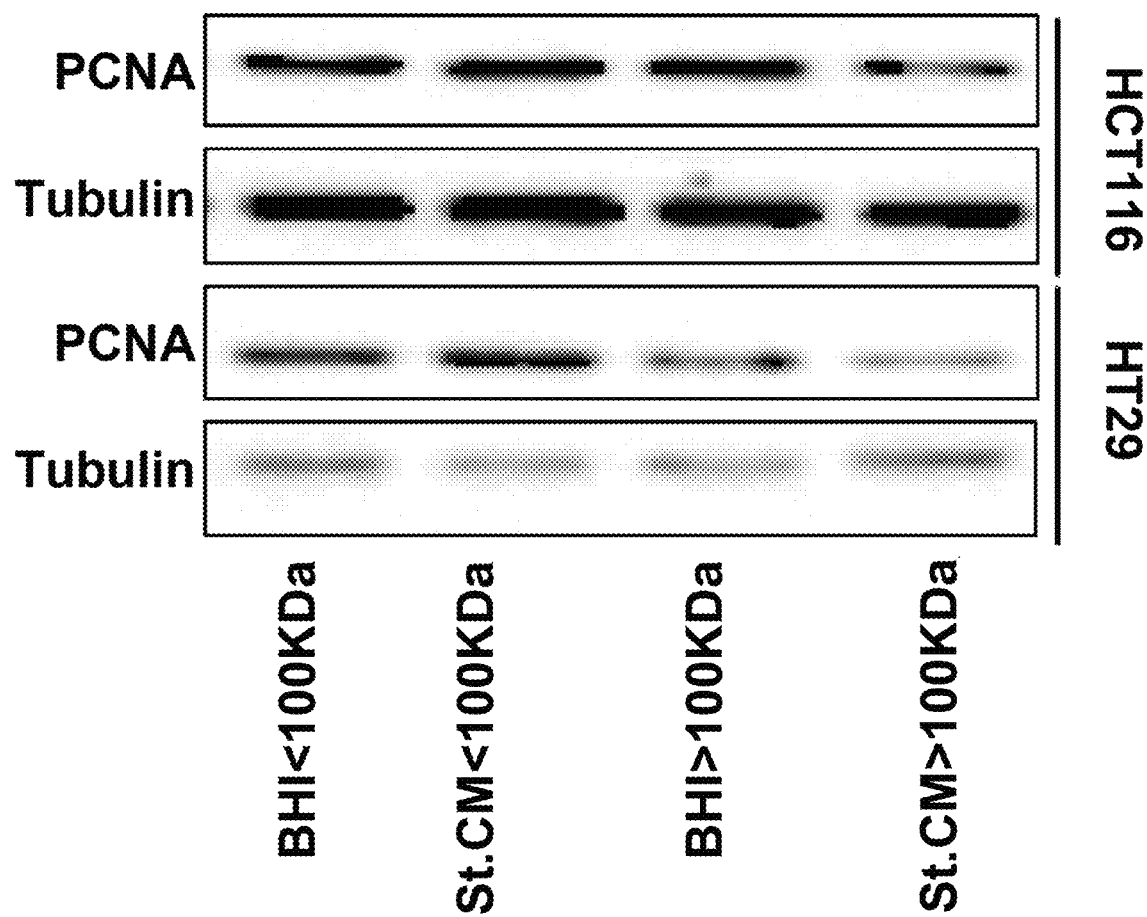
Figure 7D:
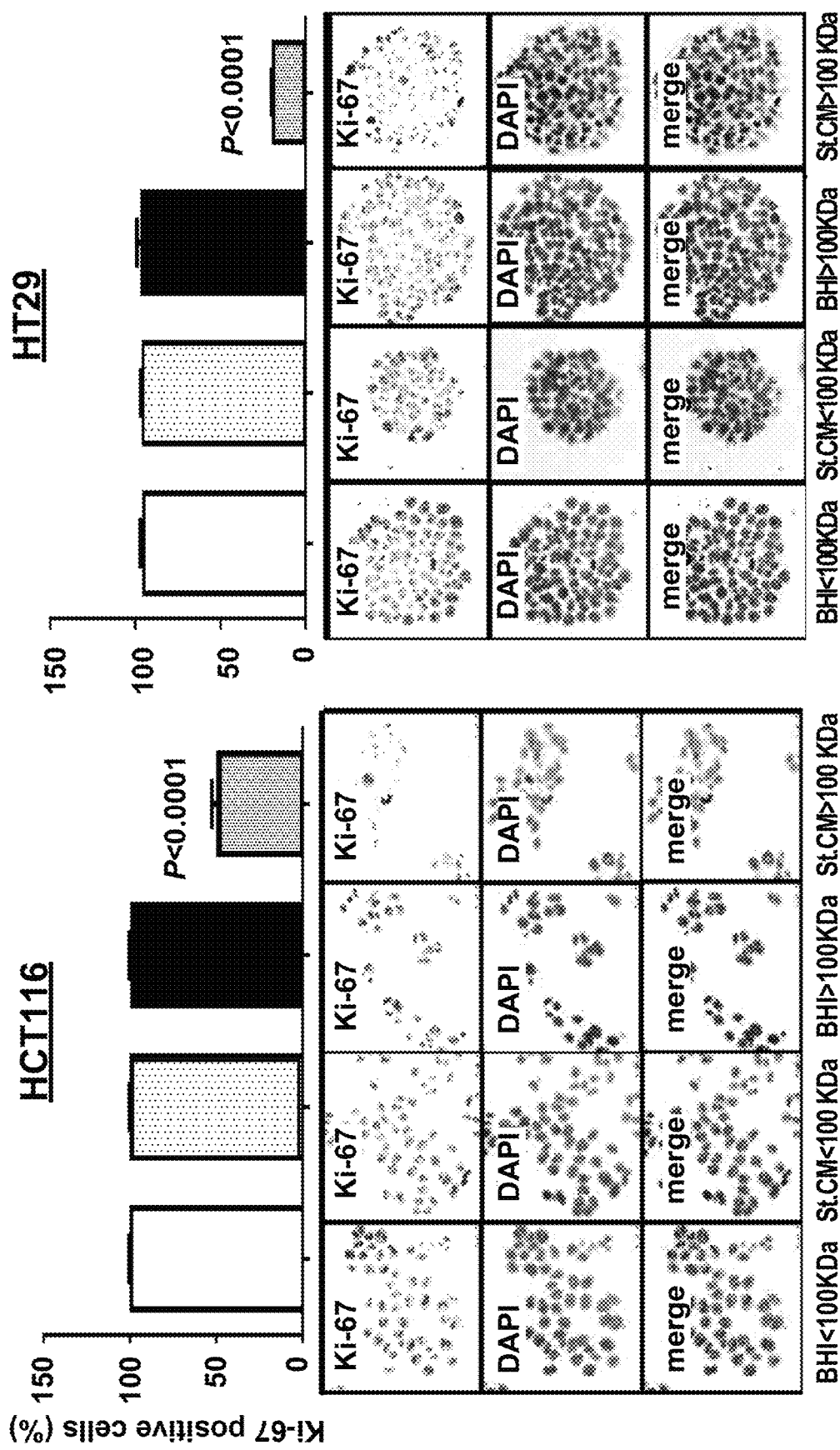

As shown in FIG. 7A, the MTT assay revealed that the St.CM>100-KDa fractions exhibited a significant anti-tumor effect, which indicate the St.CM>100-KDa molecules released from *S. thermophilus* inhibit the viability of colon cancer cells. Colony formation, proliferating cell nuclear antigen (PCNA) protein level and Ki-67 immunostaining in FIG. 7B, FIG. 7C and FIG. 7D all revealed the same results.

St.CM>100-KDa Fraction Promotes the Apoptosis of Colon Cancer Cells

Figure 8A:
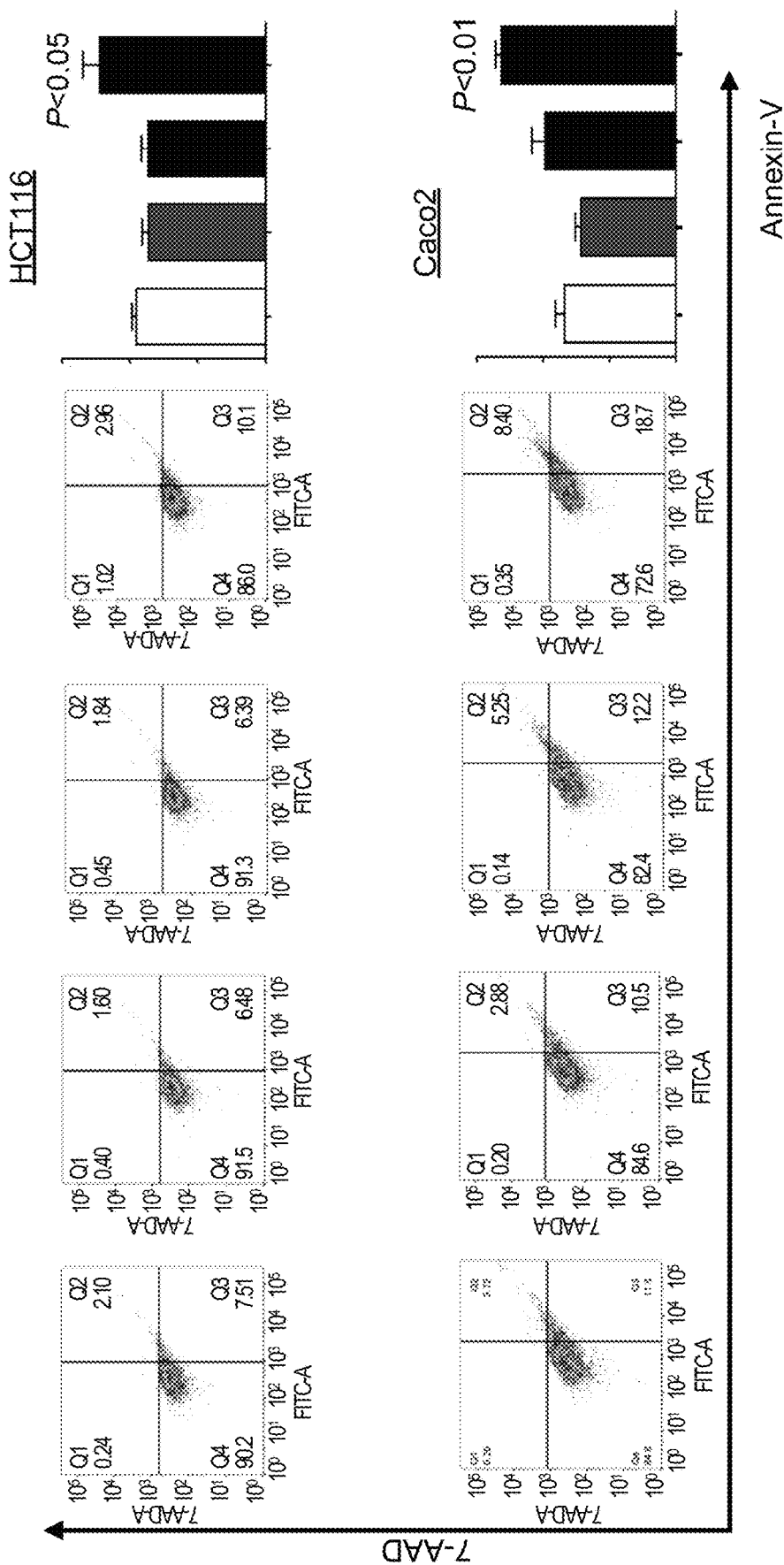
FIGS. 8A-8B shows the pro-apoptotic effect of >100 KDa fraction from St.CM in CRC cell lines.
Figure 8B:
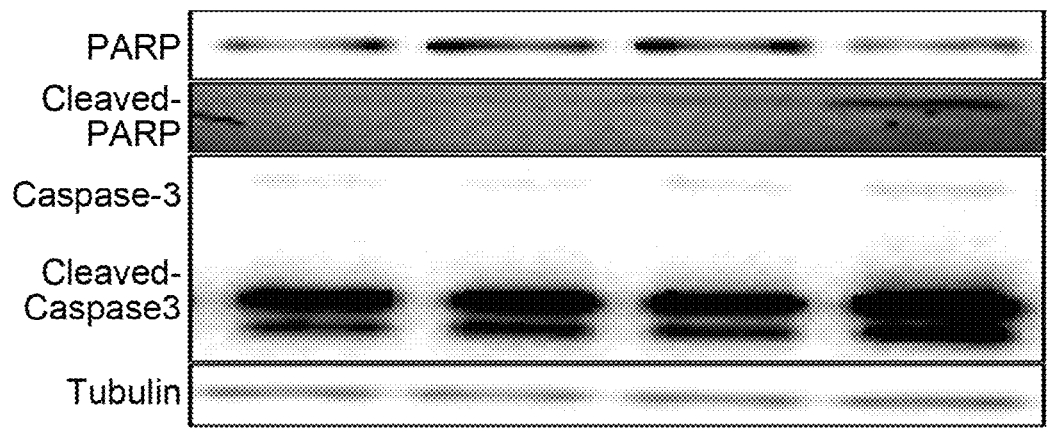
Figure 8B:
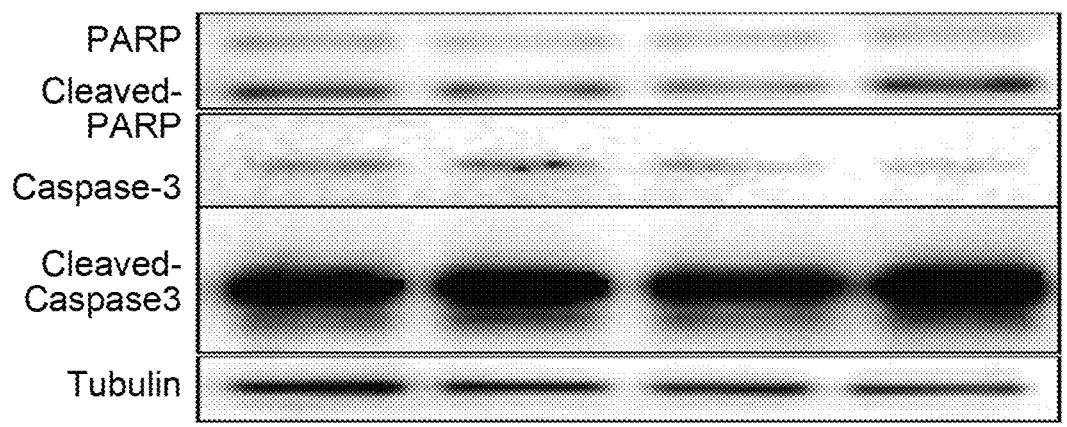

The effect of St.CM>100-KDa fraction on cell apoptosis was examined using flow cytometry after the treated cells were stained with Annexin V and propidium iodide (PI). As shown in FIG. 8A, there was a significant increase in the numbers of apoptotic cells in St.CM>100-KDa fraction-treated HCT116 cells compared with the BHI>100-KDa fraction treated group. This effect was also observed in Caco-2 cells, the proportions of apoptotic cells also significantly increased compared with the control group. Consistent with this finding, St.CM>100-KDa fraction also caused the enhancement of protein expression of cleaved-caspase 3, and cleaved poly (ADP-ribose) polymerase (PARP) in both HCT116 and HT29 cell lines (FIG. 8B). These data confirmed the inhibitory effect of St.CM>100-KDa fraction on cell viability.

St.CM>100-KDa Fraction Arrests Cell Cycle at G0/G1 Phase

Figure 9:
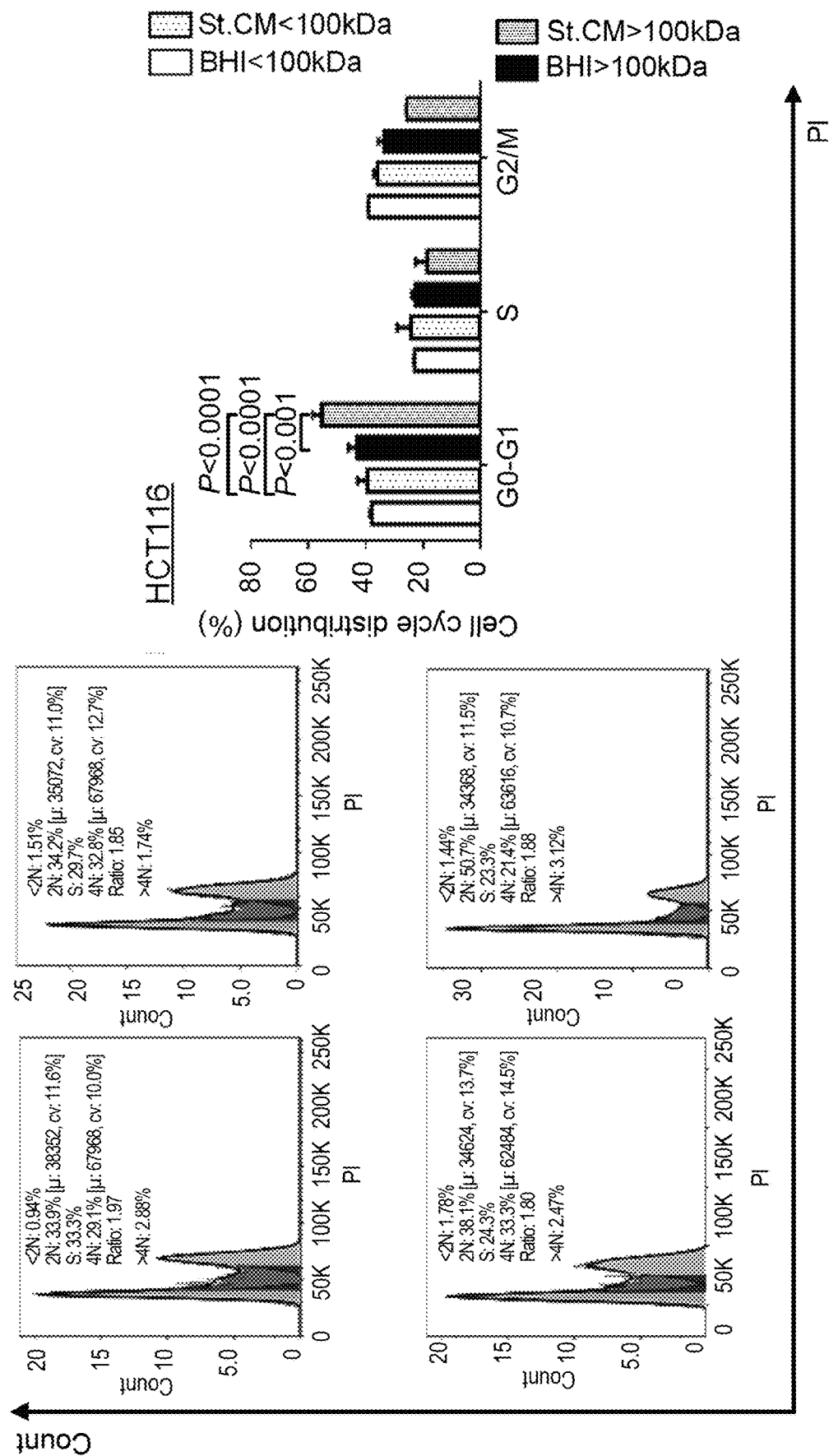
FIG. 9 shows the cell cycle-arresting effect of >100 KDa fraction from St.CM in CRC cell lines.
Figure 9:
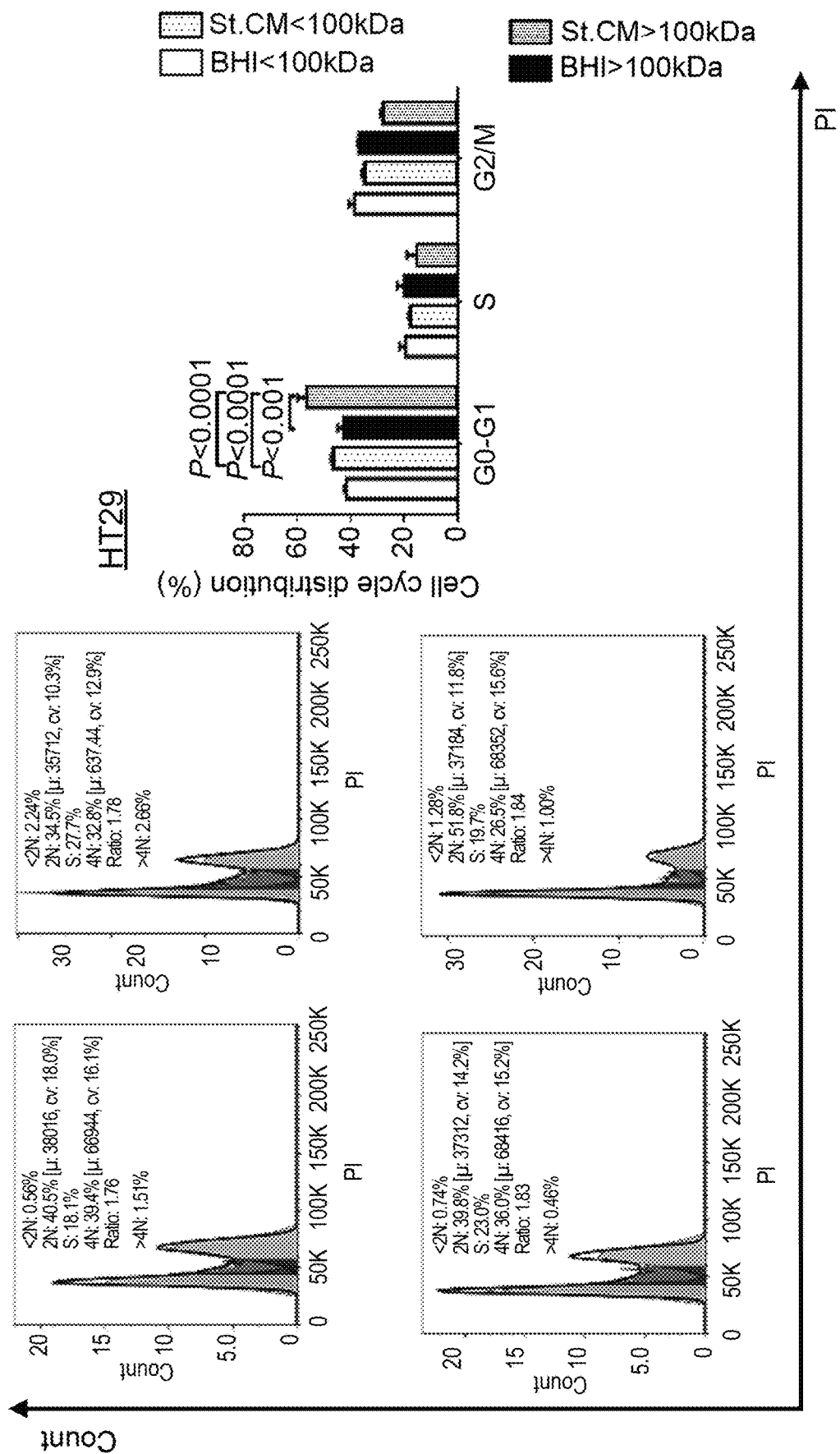

To determine the molecular mechanism by which St.CM>100-KDa fraction suppresses cell proliferation, the effect of St.CM>100-KDa fraction on cell cycle distribution was investigated by flow cytometry after propidium iodide (PI) staining. As shown in FIG. 9, treatment of St.CM>100-KDa fraction led to a decreasing tread in the number of the S and G2-phases of HCT116 and Caco-2 cells and an increase in the G0/G1 phase cells of both cell line (P<0.001). These findings indicated that apoptosis in conjunction with cell cycle arrest, as induced by St.CM>100-KDa fraction, accounts for the growth inhibition in colon cancer cells.

Figure 10:
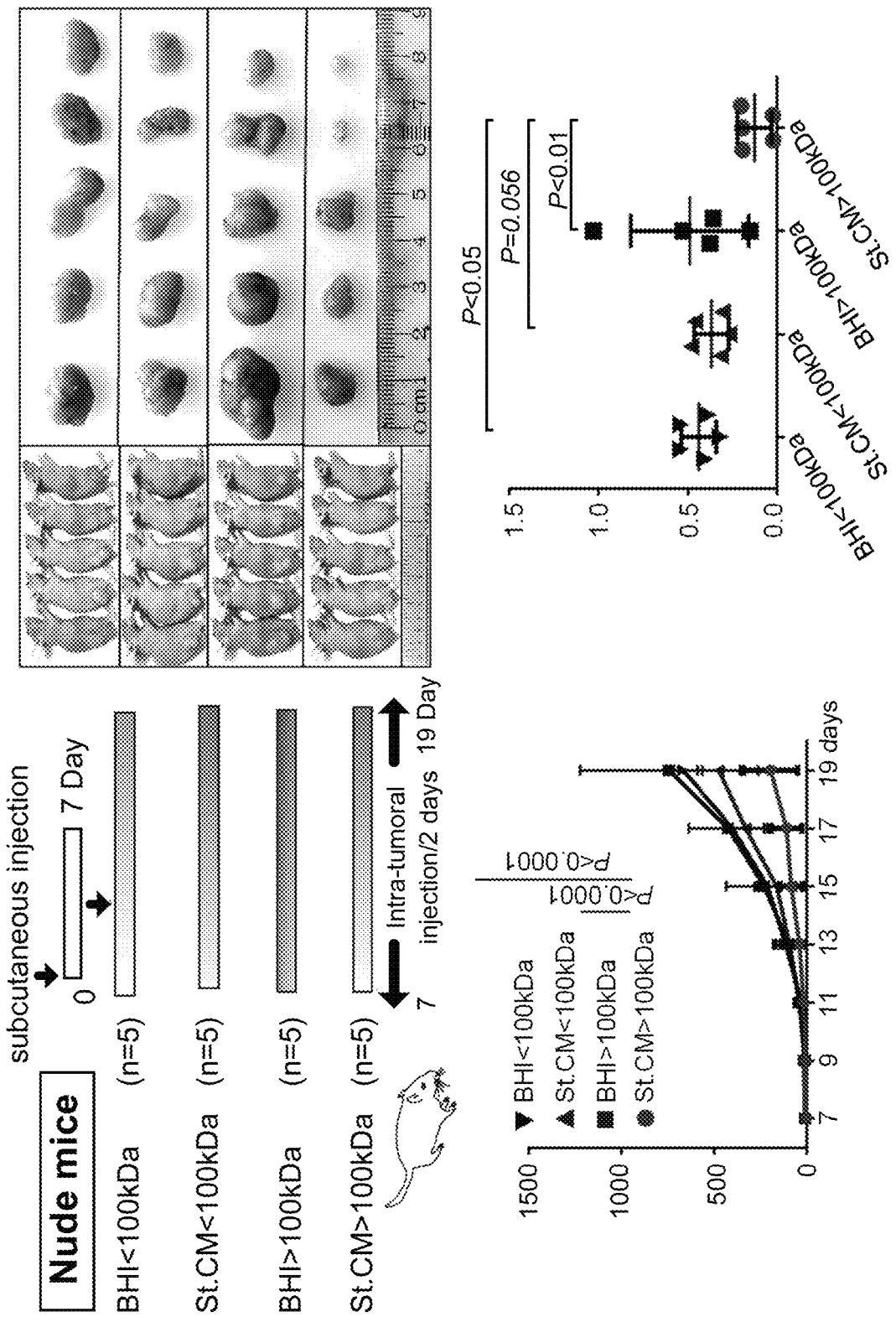
FIG. 10 shows the inhibitory effect of >100 KDa fraction from St.CM on the growth of CRC xenografts in nude mice.

St.CM>100-KDa Fraction Inhibits Tumor Growth in Nude Mice of Subcutaneous Xenograft Model To confirm the tumor-suppressive effect of St.CM>100-KDa fraction in CRC, it was tested whether St.CM>100-KDa fraction could suppress the growth of CRC cells in nude mice in vivo. A suspension of $3 \times 10^6$ of HCT116 cells were injected into the back of nude mice to build a xenograft model. After 7 days, the St.CM>100-KDa fraction was injected into the tumors. The tumor sizes were measured per two days. BHI>100-KDa, BHI<100-KDa and St.CM<100-KDa fractions were used as control treatment. As shown in FIG. 10, the tumor growth of the St.CM>100-KDa fraction-treated group was significantly slower than in those control-treated groups. Nineteen days after injection, the mice were sacrificed, and the xenografts were excised. The tumor volume was significantly lower in St.CM>100-KDa fraction-treated nude mice as compared to the control treated mice (P<0.05). The average tumor weight in the nude mice treated with St.CM>100-KDa fraction treated was significantly lower than that in the control treated mice (P<0.05). The results from the in vivo model provided further evidence of the tumor-suppressive role of St.CM>100-KDa fraction.

The Characterization of the *S. thermophilus* Secreted >100-KDa Fraction

Figure 11A:
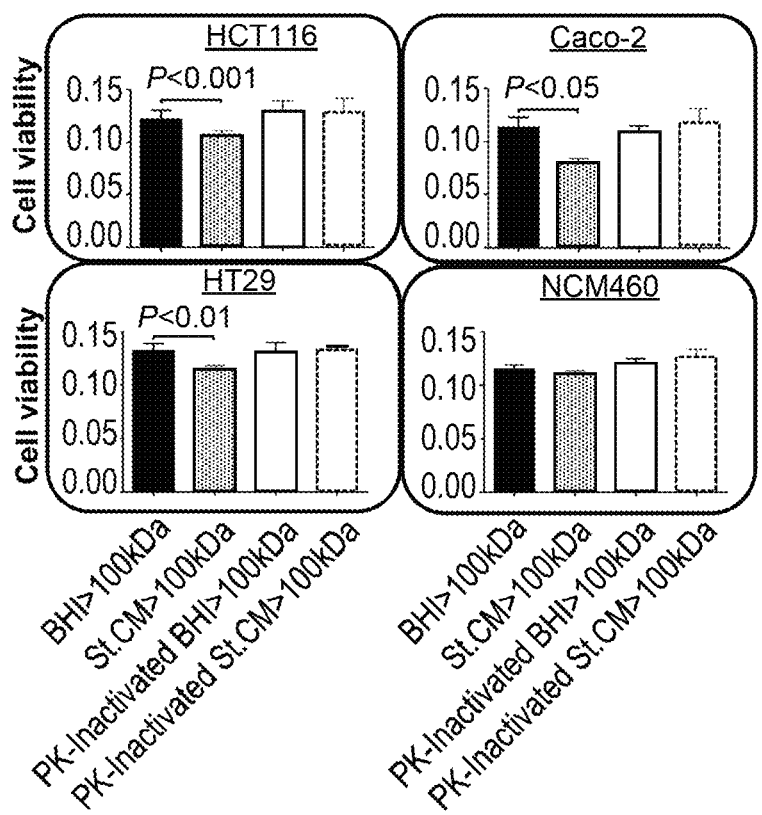
FIGS. 11A-11b shows that >100 KDa fraction from St.CM lost its inhibitory effects on the viability of CRC cell lines after heat inactivation or co-incubation with proteinase K.
Figure 11B:
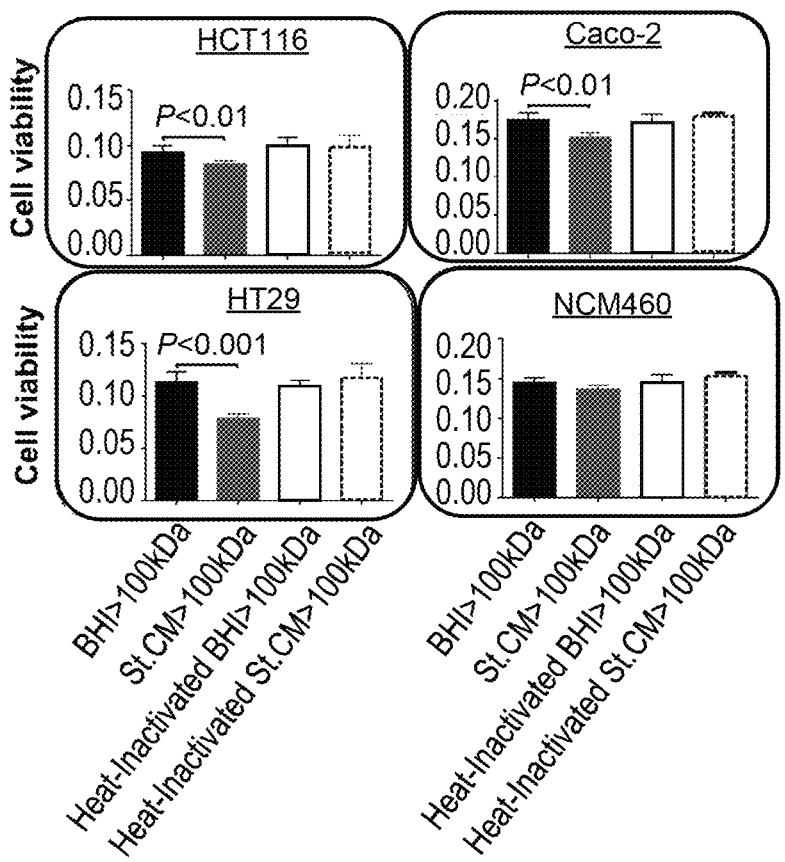

The anti-tumor compound in the St.CM>100-KDa fraction was further characterized. Firstly, the St.CM>100-KDa fractions were digested by protease K (PK, 50 μg/mL), the inhibition effect of the PK-inactivated St.CM>100-KDa fractions were assessed by MTT assay at the concentration of 1% (vol/vol) in cell growth medium for 24 hours. As shown in FIG. 11A, the inhibitory effect of St.CM>100-KDa fractions only existed in the non-digested group. In the PK-treated group, there was no significant difference between the BHI>100-KDa fraction and St.CM>100-KDa fraction, indicating that the anti-tumor molecules in the St.CM>100-KDa fraction are proteins. To further validate this result, the St.CM>100-KDa fractions were boiled in a 100° C. water bath for 30 mins to inactivate the protein in the isolated fraction. MTT assay was performed again, and the results were shown in FIG. 11B, indicating the same conclusion: the anti-tumor molecules in the St.CM>100-KDa fraction are protein.

The Identification of the Probiotic Secreted Protein

To reveal what protein or proteins have the anti-tumor effect, the secreted proteins were separated by sodium dodecyl sulfate polyacrylamide gel electrophoresis (5%)

Figure 12A:
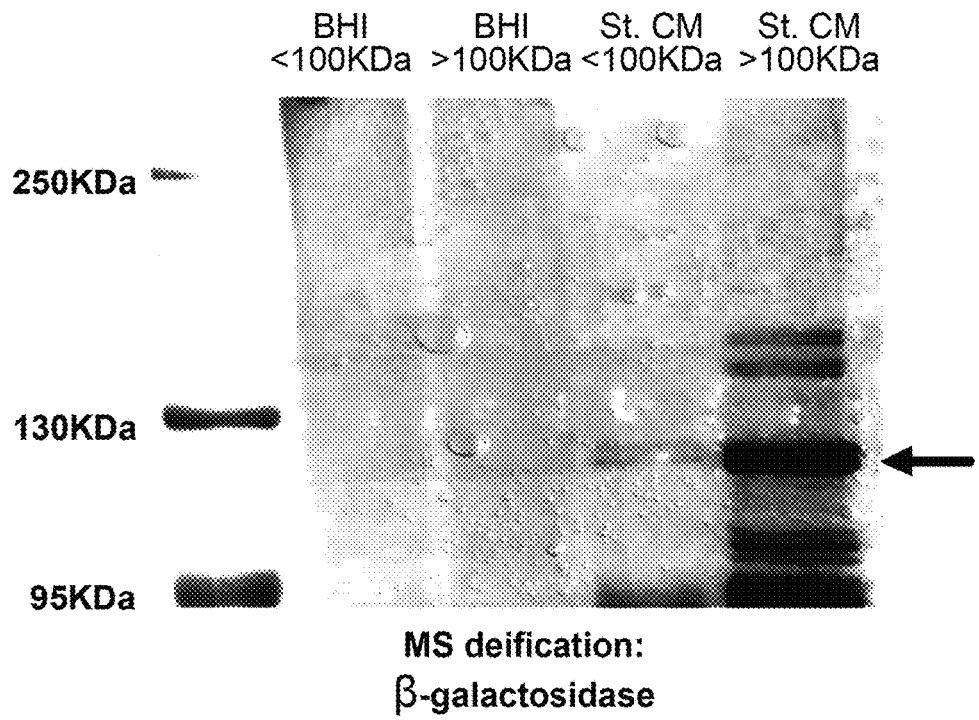
FIGS. 12A-12B shows that the tumor-suppressive fraction separated from St.CM contained β-galactosidase.
Figure 12B:
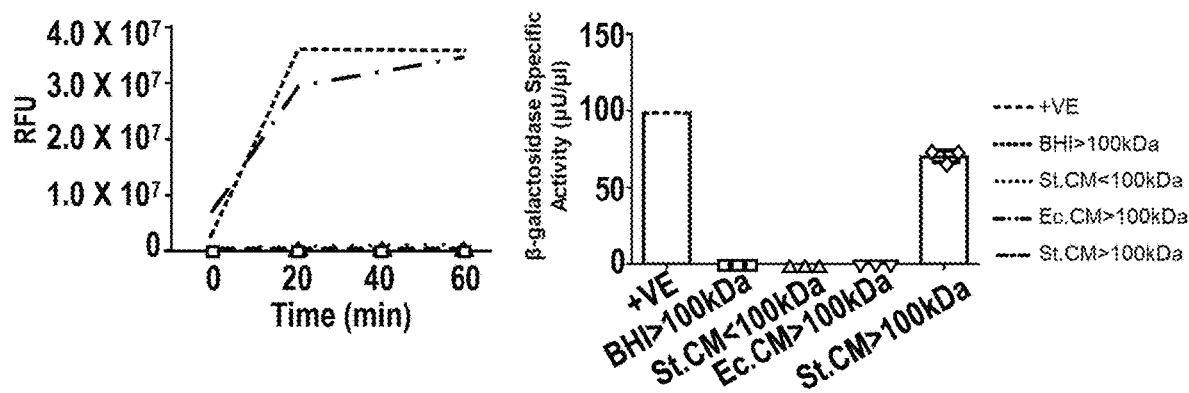

(SDS-PAGE) and recycled through in gel digestion, which was then subject to the mass spectrometry. The HPLC spectrum indicated that the protein was β-galactosidase (FIG. 12A). To validate this result, the activity of the β-galactosidase in the probiotic secreted >100-KDa fraction was determined. As shown in FIG. 12B, the activity of β-galactosidase in St.CM>100-KDa fraction was significantly higher compared with the Ec.CM, BHI>100-KDa, BHI<100-KDa and St.CM<100-KDa. These results indicate that an anti-tumor fraction separated from the St.CM contained a large amount of β-galactosidase.

Figure 13:
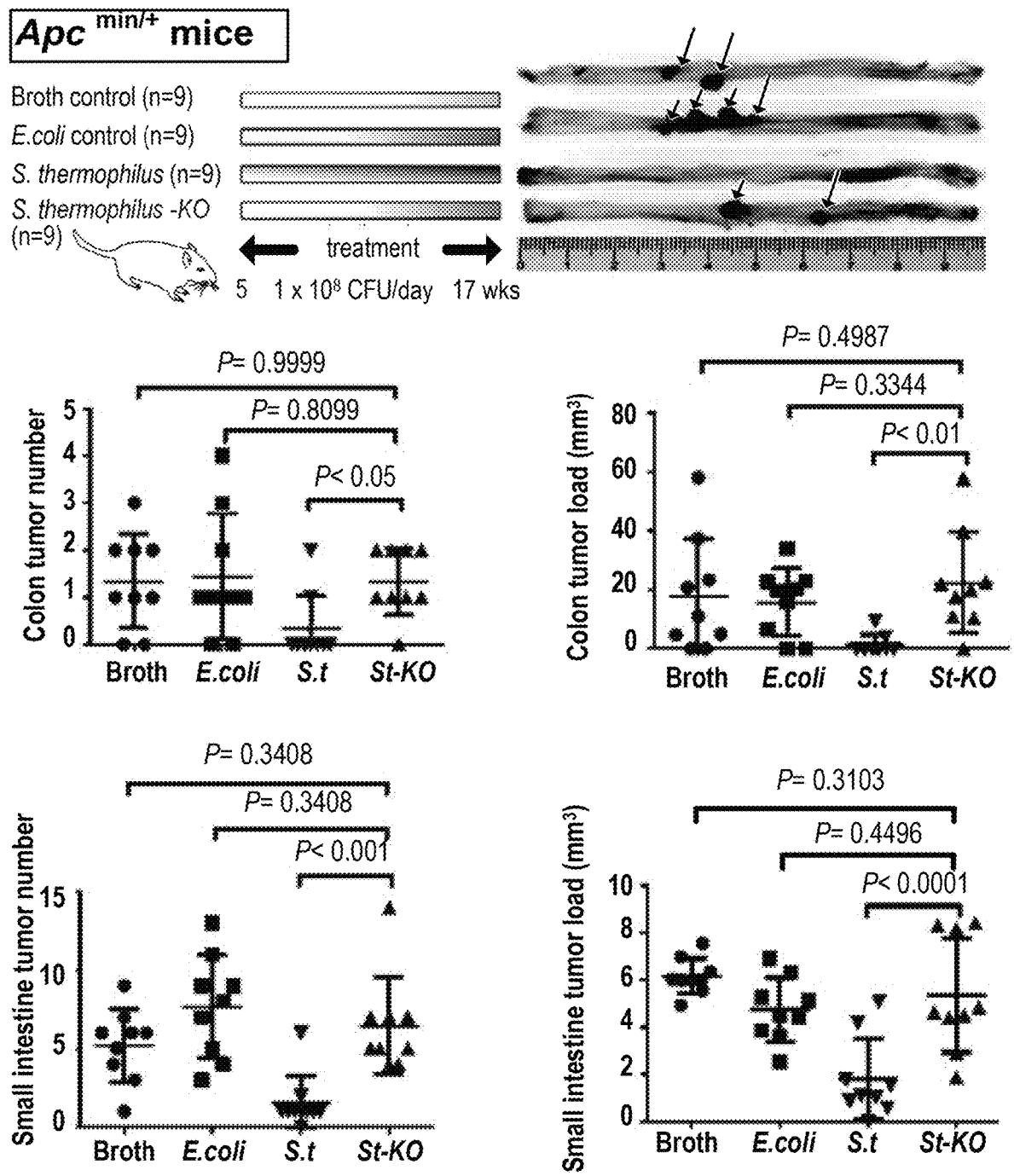
FIG. 13 shows that the anti-tumor effect of S. thermophilus is mediated by the secretion of β-galactosidase.

The Anti-Tumor Effect of *S. thermophilus* is Mediated by the Secretion of β-Galactosidase To determine the functional involvement of β-galactosidase, we constructed a mutant *S. thermophilus* strain (LacZ knockout) by homologous recombination. which will cause the functionally abolish the production of β-galactosidase from *S. thermophilus*. As shown in FIG. 13, oral gavage of LacZ-knockout *S. thermophilus* (ST-KO) into $Apc^{min/+}$ mice failed to protect against intestinal tumorigenesis (P>0.05), indicating that the anti-tumor effect of *S. thermophilus* is mediated by the secretion of β-galactosidase.

All patents, patent applications, and other publications, including GenBank Accession Numbers or equivalents, cited in this application are incorporated by reference in the entirety for all purposes.

LIST OF REFERENCES

1. Siegel R L, Miller K D, Jemal A. Cancer Statistics, 2017. CA: a cancer journal for clinicians. January 2017; 67(1): 7-30.
2. Siegel R L, Miller K D, Fedewa S A, et al. Colorectal cancer statistics, 2017. CA: a cancer journal for clinicians. May 6, 2017; 67(3): 177-193.
3. Daniel S G, Ball C L, Besselsen D G, Doetschman T, Hurwitz B L. Functional Changes in the Gut Microbiome Contribute to Transforming Growth Factor beta-Deficient Colon Cancer. mSystems. September-October 2017; 2(5).
4. Healy A R, Herzon S B. Molecular Basis of Gut Microbiome-Associated Colorectal Cancer: A Synthetic Perspective. Journal of the American Chemical Society. Oct. 12, 2017.
5. Purcell R V, Visnovska M, Biggs P J, Schmeier S, Frizelle F A. Distinct gut microbiome patterns associate with consensus molecular subtypes of colorectal cancer. Scientific reports. Sep. 14, 2017; 7(1):11590.
6. Golombos D M, Ayangbesan A, O'Malley P, et al. The Role of Gut Microbiome in the Pathogenesis of Prostate Cancer: a Prospective, Pilot Study. Urology. Sep. 6, 2017.
7. Vogtmann E, Hua X, Zeller G, et al. Colorectal Cancer and the Human Gut Microbiome: Reproducibility with Whole-Genome Shotgun Sequencing. PloS one. 2016; 11(5):e0155362.
8. Denipote F G, Trindade E B, Burini R C. [Probiotics and prebiotics in primary care for colon cancer]. Arquivos de gastroenterologia. January-March 2010; 47(1):93-98.
9. Ohara T, Yoshino K, Kitajima M. [Pre- and probiotics increase host-cell immunological competence, improve bowel movement, and prevent the onset of colon cancer—an analysis based on movements of intestinal microbiota]. Rinsho byori. The Japanese journal of clinical pathology. June 2009; 57(6):533-541.
10. Liong M T. Roles of probiotics and prebiotics in colon cancer prevention: Postulated mechanisms and in-vivo evidence. International journal of molecular sciences. May 2008; 9(5):854-863.
11. Roller M, Clune Y, Collins K, Rechkemmer G, Watzl B. Consumption of prebiotic inulin enriched with oligofructose in combination with the probiotics Lactobacillus rhamnosus and *Bifidobacterium lactis* has minor effects on selected immune parameters in polypectomised and colon cancer patients. The British journal of nutrition. April 2007; 97(4):676-684.

What is claimed is:

1. A method for suppressing colon cancer cell proliferation, comprising the step of contacting colon cancer cells with an extract of a *S. thermophilus* culture that is essentially free of *S. thermophilus* and retaining only components with a molecular weight of 100 kDa or greater.

2. The method of claim 1, wherein the extract is a *S. thermophilus* culture essentially free of *S. thermophilus* retained on a membrane with a molecular weight cut-off (MWCO) of 100 kDa following filtration.

3. The method of claim 1, wherein the colon cancer cells are within a subject's body.

4. The method of claim 3, wherein the subject has a family history of colon cancer but has not been diagnosed with colon cancer.

5. The method of claim 3, wherein the subject has been diagnosed with colon cancer.

6. The method of claim 3, wherein the subject is orally administered the extract.

7. The method of claim 6, wherein the extract is a *S. thermophilus* culture essentially free of *S. thermophilus* retained on a membrane with a molecular weight cut-off (MWCO) of 100 kDa following filtration.

8. The method of claim 1, further comprising contacting the cancer cells with an effective amount of an anti-cancer therapeutic agent.

9. The method of claim 8, wherein the anti-cancer therapeutic agent is present in one composition with the extract.

10. The method of claim 9, wherein the anti-cancer therapeutic agent is present in a composition separate from the extract.

11. The method of claim 6, further comprising orally administering to the subject an effective amount of an anti-cancer therapeutic agent.

12. The method of claim 11, wherein the anti-cancer therapeutic agent is administered to the subject in one composition with the extract.

13. The method of claim 12, wherein the anti-cancer therapeutic agent is administered to the subject in a composition separate from the extract.

* * * * *